(12) United States Patent
Feldman et al.

(10) Patent No.: US 7,783,337 B2
(45) Date of Patent: Aug. 24, 2010

(54) OCT USING SPECTRALLY RESOLVED BANDWIDTH

(75) Inventors: Marc D. Feldman, San Antonio, TX (US); Thomas E. Milner, Austin, TX (US); Jung Hwan Oh, Austin, TX (US); Eunha Kim, Austin, TX (US); Karthik Kumar, Austin, TX (US); Chris Condit, Austin, TX (US); Robert Grant, Austin, TX (US); Nate Kemp, Austin, TX (US); Jeehyun Kim, Irvine, CA (US); Shaochen Chen, Austin, TX (US); Li-Hsin Han, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1055 days.

(21) Appl. No.: 11/446,683

(22) Filed: Jun. 5, 2006

(65) Prior Publication Data

US 2007/0015969 A1 Jan. 18, 2007

Related U.S. Application Data

(60) Provisional application No. 60/687,930, filed on Jun. 6, 2005.

(51) Int. Cl.
*A61B 5/05* (2006.01)
(52) U.S. Cl. .................................. 600/407; 600/160
(58) Field of Classification Search ............... 600/117, 600/407, 476, 160; 382/128, 154
See application file for complete search history.

(56) References Cited

U.S. PATENT DOCUMENTS

| | | | | |
|---|---|---|---|---|
| 5,106,387 A | * | 4/1992 | Kittrell et al. | 606/15 |
| 5,266,811 A | * | 11/1993 | Matsuura | 250/559.23 |
| 5,873,822 A | * | 2/1999 | Ferre et al. | 600/407 |
| 6,134,003 A | * | 10/2000 | Tearney et al. | 356/479 |

(Continued)

FOREIGN PATENT DOCUMENTS

WO 2004/096049 11/2004

OTHER PUBLICATIONS

Macilwain, Colin, "US plans large funding boost to support nanotechnology boom", *Nature*, vol. 400, pp. 1 (Jul. 8, 1999).

(Continued)

*Primary Examiner*—John P Leubecker
*Assistant Examiner*—Samuel Candler
(74) *Attorney, Agent, or Firm*—J. Peter Paredes; Rosenbaum & Silvert, P.C.

(57) ABSTRACT

An apparatus is disclosed for studying an object based on at least one of polarization, space, position or angle of light that has reflected from the object. An optical tomographic instrumentation of the apparatus includes a light source coupled to a source path, a sample path, a reference path, and a detection path, wherein the light source generates a spectrally resolved bandwidth. The spectrally resolved bandwidth includes a plurality of spectrally resolved cells and a detector in the detection path for analyzing light reflected from an object in the sample path and the light reflected in the reference path based upon at least one of the polarization, spatial relationship, position or angle domains.

25 Claims, 23 Drawing Sheets

U.S. PATENT DOCUMENTS

| | | | | |
|---|---|---|---|---|
| 6,134,033 | A | 10/2000 | Bergano et al. | 359/122 |
| 6,208,415 | B1 | 3/2001 | De Boer et al. | 356/351 |
| 6,442,417 | B1* | 8/2002 | Shahidi et al. | 600/429 |
| 6,501,551 | B1 | 12/2002 | Tearney et al. | 356/477 |
| 6,574,355 | B2* | 6/2003 | Green | 382/128 |
| 6,704,106 | B2* | 3/2004 | Anderson et al. | 356/367 |
| 6,943,881 | B2* | 9/2005 | Wang | 356/369 |
| 7,126,693 | B2* | 10/2006 | Everett et al. | 356/479 |
| 7,144,367 | B2* | 12/2006 | Chen et al. | 600/117 |
| 7,177,491 | B2 | 2/2007 | Dave et al. | 385/11 |
| 7,211,042 | B2* | 5/2007 | Chatenever et al. | 600/117 |
| 7,258,664 | B2* | 8/2007 | Nishimura et al. | 600/117 |
| 7,511,731 | B2* | 3/2009 | Katayama et al. | 348/42 |
| 7,595,879 | B2* | 9/2009 | Wang | 356/369 |
| 7,604,589 | B2* | 10/2009 | Glukhovsky et al. | 600/117 |
| 2003/0040668 | A1* | 2/2003 | Kaneko et al. | 600/407 |
| 2003/0223064 | A1* | 12/2003 | Anderson et al. | 356/364 |
| 2004/0126048 | A1* | 7/2004 | Dave et al. | 385/11 |
| 2005/0015005 | A1* | 1/2005 | Kockro | 600/427 |
| 2005/0054895 | A1* | 3/2005 | Hoeg et al. | 600/117 |
| 2005/0090751 | A1* | 4/2005 | Balas | 600/476 |
| 2005/0107666 | A1* | 5/2005 | Glukhovsky et al. | 600/117 |
| 2005/0123179 | A1* | 6/2005 | Chen et al. | 382/128 |
| 2005/0213103 | A1* | 9/2005 | Everett et al. | 356/479 |
| 2007/0015969 | A1 | 1/2007 | Feldman et al. | 600/160 |

OTHER PUBLICATIONS

Polla, D., et al., "Microdevices in Medicine", *Annu. Rev. Biomed. Eng.*, vol. 2, pp. 551-576 (2000).

McAllister, D.V., et al., "Microfabricated Microneedles for Gene and Drug Delivery", *Annu. Rev. Biomed. Eng.*, vol. 2, pp. 289-313 (2000).

Zheng, W., et al., "Micro-Manufacturing of a Nano-Liter-Scale, Continuous Flow Polymerase Chain Reaction System", *Transactions of NAMRI/SME*, vol. XXX, pp. 551-556, (2002).

Kancharla, V., et al., "Fabrication of Biodegradable Polymeric Micro-Devices Using Laser Micromachining", *Biomedical Microdevices*, vol. 4, No. 2, pp. 105-109, (2002).

Chen, S.C., et al., "Melting and Surface Deformation in Pulsed Laser Surface Micromodification of Ni-P Disks", *Journal of Heat Transfer*, vol. 122, pp. 107-112, (Feb. 2000).

Nisssen, S., "Coronary Angiography and Intravascular Ultrasound", *Am J Cardiol*, vol. 87, pp. 15A-20A, (Feb. 16, 2001).

Davies, M., et al., "Plaque Fissuring—the cause of acute myocardial infarction, sudden ischaemic death, and crescendo angina", *Br Heart J*, vol. 53, pp. 363-373, (1985).

Davies, M., et al., "Risk of thrombosis in human atherosclerotic plaques; role of extracellular lipid, macrophage, and smooth muscle cell content", *Br Heart J.*, vol. 69, pp. 377-381, (1993).

Rabbani, R., et al., "Strategies to achieve coronary arterial plaque stabilization", Cardiovascular Research, vol. 41, pp. 402-417, (1999).

Villard, J.W., et al., "Use of a Blood Substitute to Determine Instantaneous Murine Right Ventricular Thickening With Optical Coherence Tomography", *Circulation*, vol. 105, pp. 1843-1849 (Apr. 1, 2002).

Jang, I-K, et al., "Visualization of Coronary Atherosclerotic Plaques in Patients Using Optical Coherence Tomography: Comparison With Intravascular Ultrasound", Journal of the American College of Cardiology, vol. 29, No. 4, pp. 604-609, (2002).

Feldchtein, F.I., et al., "Endoscopic applications of optical coherence tomography", *Optics Express*, vol. 3, No. 6, pp. 257-270, (Sep. 14, 1998).

Tearney, G.J., et al., "Endoscopic optical coherence tomography", *Proc SPIE—Int. Soc. Opt. Eng.*, vol. 2979, pp. 2-5, (1997).

Jesser, C.A., et al., "High resolution imaging of transitional cell carcinoma with optical coherence tomography: feasibility for the evaluation of bladder pathology", *The British Journal of Radiology*, vol. 72, pp. 1170-1176, (1999).

Feldchtein, V.M, et al., "Design and performance of an endoscopic OCT system for in vivo studies of human mucosa", *Technical Digest for Summaries of Papers—Conference on Lasers and Electro-Optics Conference Edition, Technical Digest Series*, vol. 6., pp. 122-123, (1998).

Little, et al., "The underlying coronary lesion in myocardial infarction: implications for coronary angiography", *Clin Cardiol.*, vol. 14, pp. 868-874, (1991) (Abstract only).

Optical Cable Corp homepage, http://www.occfiber.com.

Chen, S., et al., "Laser-based microscale patterning of biodegradable polymers for biomedical applications", *International Journal of Materials and Product Technology*, vol. 18, No. 4/5/6, pp. 457-468 (2003).

Volker, W., et al., "Real-time, high velocity-resolution color Doppler optical coherence tomography", *Optics Letters*, vol. 27, No. 1, pp. 34-36, (2002) (Abstract Only).

Rollins, A.M., et al., "Real-time in vivo imaging of human gastrointestinal ultrastructure by use of endoscopic optical coherence tomography with a novel efficient interferometer design", *Optics Letters*, vol. 24, No. 19, pp. 1358-1360 (1999) (Abstract Only).

PCT International Search Report, pp. 1-3 (Jun. 17, 2009).

PCT Written Opinion, pp. 1-5 (Jun. 17, 2009).

* cited by examiner

S1: BROADBAND LOW COHERENCE LIGHT SOURCE
C1: CONNECTOR 1
L1: CIRCULAR LENS
CL1, 2: CYLINDRICAL LENS
ML1: MICRO LENS ARRAY

S1: BROADBAND LOW COHERENT LIGHT SOURCE
SP1: FIBER BASED BEAM SPLITTER (1*2)
SP2, 3: FIBER BASED

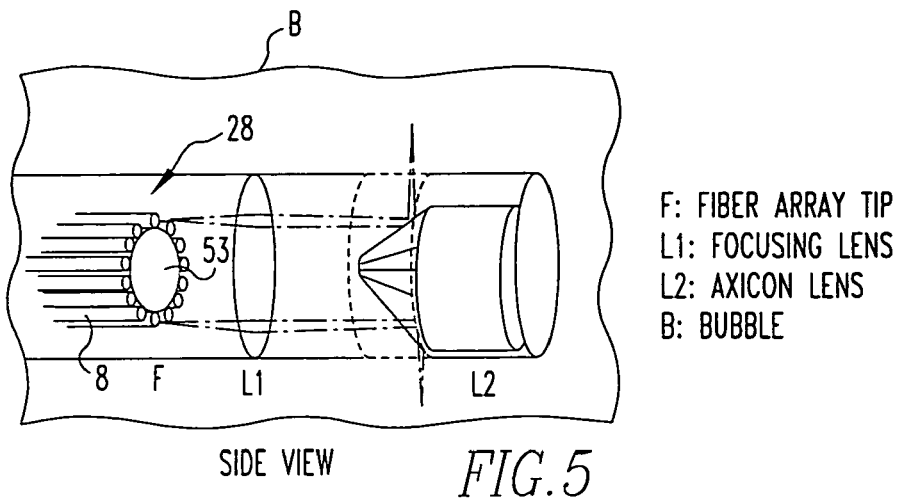
F: FIBER ARRAY TIP
L1: FOCUSING LENS
L2: AXICON LENS
B: BUBBLE
SIDE VIEW *FIG.5*
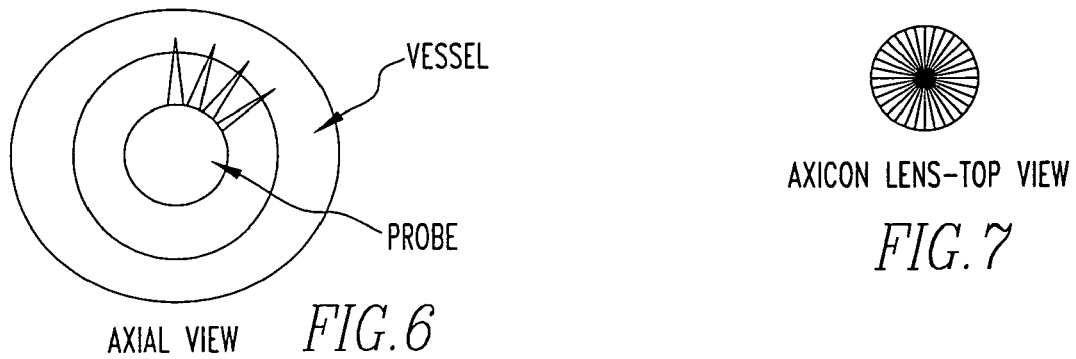
AXIAL VIEW *FIG.6*
AXICON LENS-TOP VIEW
*FIG.7*
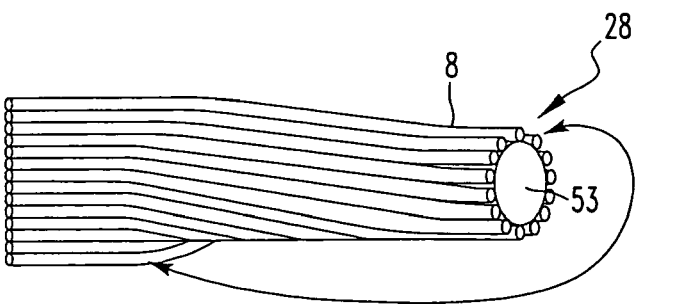
ENDOSCOPIC LINEAR TO ANNULAR OPTICAL FIBER ARRAY
*FIG.8*

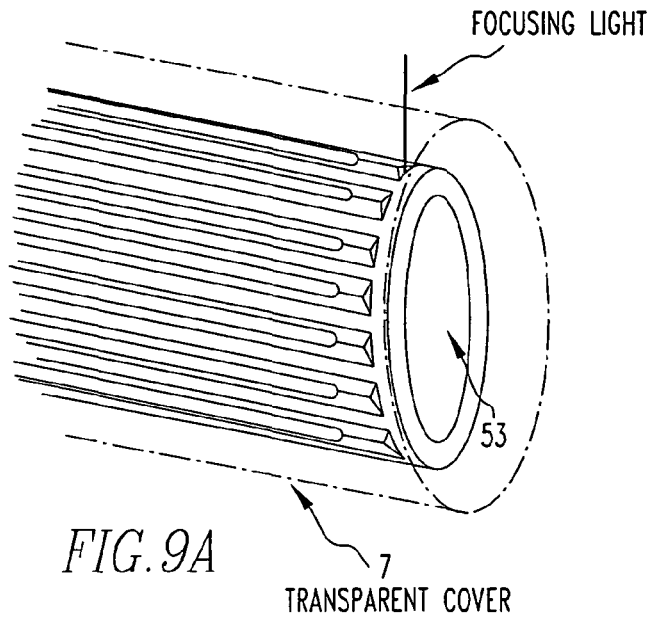
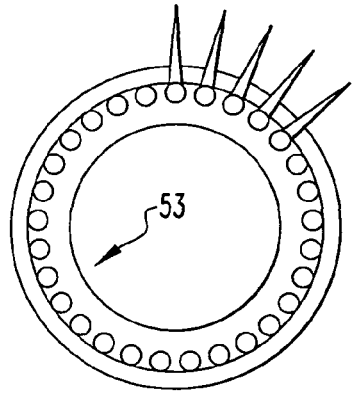
FIG.9A
FIG.9B
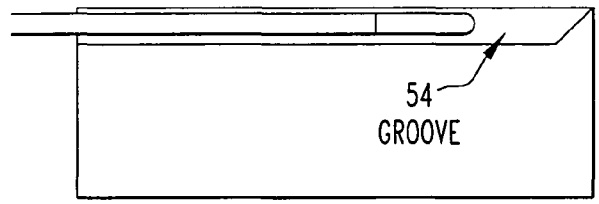
FIG.10
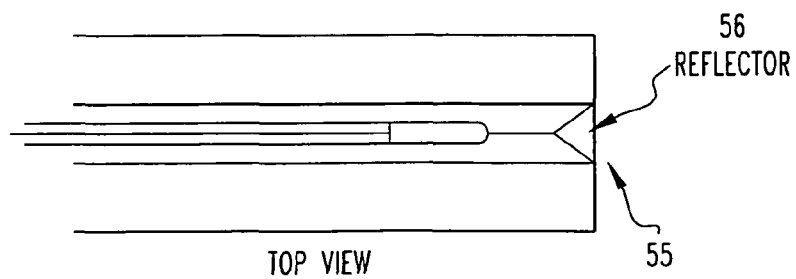
FIG.11

C4: CONNECTOR 4
L1, 2: CIRCULAR LENS
M1, 2: MIRROR
G1: GRATING
GA1: GALVONOMETER

RAPID SCAN DELAY LINE

TOP VIEW

C1: CONNECTOR 1
L1: CIRCULAR LENS
CL1, 2: CYLINDRICAL LENS
ML1: MICRO-LENS ARRAY
D: ARRAY DETECTOR

SIDE VIEW

C1: CONNECTOR 1
L1: CIRCULAR LENS
CL1, 2: CYLINDRICAL LENS
ML1: MICRO-LENS ARRAY
D: ARRAY DETECTOR

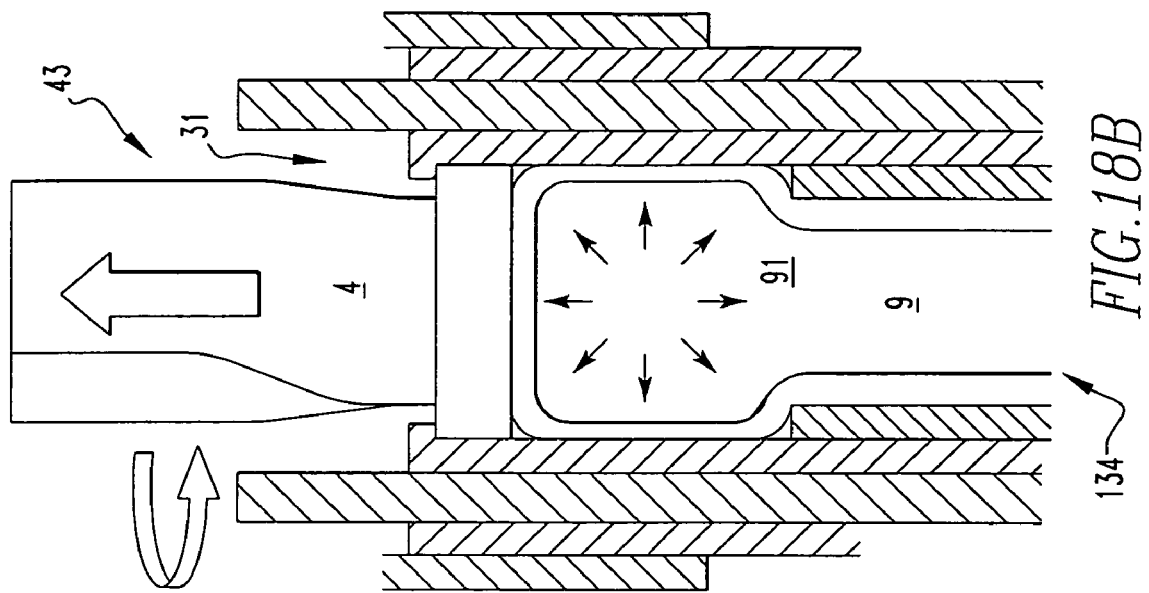
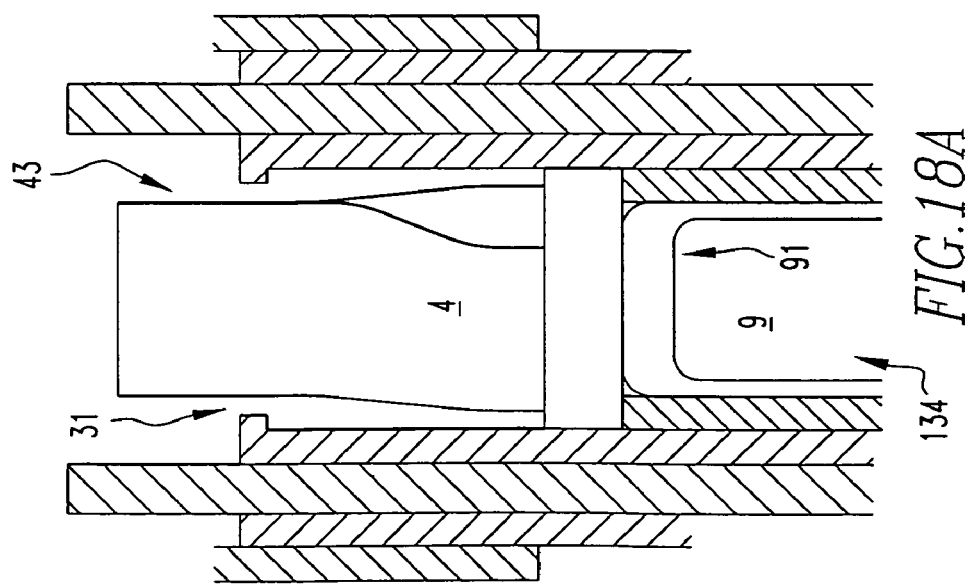

216
BASE

210
MIRROR

FIBER 2

FIBER 1 d

MIRROR'S
CENER

DETECTING
LASER alfa

FIBER 1

OCT USING SPECTRALLY RESOLVED BANDWIDTH

CROSS-REFERENCE TO RELATED APPLICATIONS

This application claims priority from Provisional Application Ser. No. 60/687,930, filed Jun. 6, 2005.

FIELD OF THE INVENTION

The present invention is related to a system for optical coherence tomographic imaging of turbid (i.e., scattering) materials utilizing multiple channels of information. The multiple channels of information may be comprised and encompass spatial, angle, spectral and polarization domains. More specifically, the present invention is related to methods and apparatus utilizing optical sources, systems or receivers capable of providing (source), processing (system) or recording (receiver) a multiplicity of channels of spectral information for optical coherence tomographic imaging of turbid materials. In these methods and apparatus the multiplicity of channels of spectral information that can be provided by the source, processed by the system, or recorded by the receiver are used to convey simultaneously spatial, spectral or polarimetric information relating to the turbid material being imaged tomographically.

The multichannel optical coherence tomographic methods can be incorporated into an endoscopic probe for imaging a patient. The endoscope comprises an optical fiber array and can comprise a plurality of optical fibers adapted to be disposed in the patient. The optical fiber array transmits the light from the light source into the patient, and transmits the light reflected by the patient out of the patient. The plurality of optical fibers in the array are in optical communication with the light source. The multichannel optical coherence tomography system comprises a detector for receiving the light from the array and analyzing the light. The methods and apparatus may be applied for imaging a vessel, biliary, GU and/or GI tract of a patient.

BACKGROUND OF THE INVENTION

Myocardial infarction or heart attack remains the leading cause of death in our society. Unfortunately, most of us can identify a family member or close friend that has suffered from a myocardial infarction. Until recently many investigators believed that coronary arteries critically blocked with atherosclerotic plaque that subsequently progressed to total occlusion was the primary mechanism for myocardial infarction. Recent evidence from many investigational studies, however, clearly indicate that most infarctions are due to sudden rupture of non-critically stenosed coronary arteries due to sudden plaque rupture. For example, Little and coworkers (Little, W C, Downes, T R, Applegate, R J. The underlying coronary lesion in myocardial infarction: implications for coronary angiography. *Clin Cardiol* 1991; 14: 868-874, incorporated by reference herein) observed that approximately 70% of patients suffering from an acute plaque rupture were initiated on plaques that were less than 50% occluded as revealed by previous coronary angiography. This and similar observations have been confirmed by other investigators (Nissen, S. Coronary angiography and intravascular ultrasound. *Am J Cardiol* 2001; 87 (suppl): 15A-20A, incorporated by reference herein).

The development of technologies to identify these unstable plaques holds the potential to decrease substantially the incidence of acute coronary syndromes that often lead to premature death. Unfortunately, no methods are currently available to the cardiologist that may be applied to specify which coronary plaques are vulnerable and thus prone to rupture. Although treadmill testing has been used for decades to identify patients at greater cardiovascular risk, this approach does not have the specificity to differentiate between stable and vulnerable plaques that are prone to rupture and frequently result in myocardial infarction. Inasmuch as a great deal of information exists regarding the pathology of unstable plaques (determined at autopsy) technologies based upon identifying the well described pathologic appearance of the vulnerable plaque offers a promising long term strategy to solve this problem.

The unstable plaque was first identified and characterized by pathologists in the early 1980's. Davis and coworkers noted that with the reconstruction of serial histological sections in patients with acute myocardial infarctions associated with death, a rupture or fissuring of atheromatous plaque was evident (Davis M J, Thomas A C. Plaque fissuring: the cause of acute myocardial infarction, sudden death, and crescendo angina. *Br Heart J* 1985; 53: 363-373, incorporated by reference herein). Ulcerated plaques were further characterized as having a thin fibrous cap, increased macrophages with decreased smooth muscle cells and an increased lipid core when compared to non-ulcerated atherosclerotic plaques in human aortas (Davis M J, Richardson P D, Woolf N, Katz D R, Mann J. Risk of thrombosis in human atherosclerotic plaques: role of extracellular lipid, macrophage, and smooth muscle cell content, incorporated by reference herein). Furthermore, no correlation in size of lipid pool and percent stenosis was observed when imaging by coronary angiography. In fact, most cardiologists agree that unstable plaques progress to more stenotic yet stable plaques through progression via rupture with the formation of a mural thrombus and plaque remodeling, but without complete luminal occlusion (Topol E J, Rabbaic R. Strategies to achieve coronary arterial plaque stabilization. *Cardiovasc Res* 1999; 41: 402-417, incorporated by reference herein). Neo-vascularization with intra-plaque hemorrhage may also play a role in this progression from small lesions (<50% occluded) to larger significant plaques. Yet, if the unique features of unstable plaque could be recognized by the cardiologist and then stabilized, a dramatic decrease may be realized in both acute myocardial infarction and unstable angina syndromes, and in the sudden progression of coronary artery disease.

The present invention uses depth-resolved light reflection or Optical Coherence Tomography (OCT) to identify the pathological features that have been identified in the vulnerable plaque. In OCT, light from a broad band light source or tunable laser source is input into an interferometer with a portion of light directed to the vessel wall and the other portion directed to a reference surface. The distal end of the optical fiber is interfaced with a catheter for interrogation of the coronary artery during a heart catheterization procedure. The reflected light from the plaque is recombined with the signal from the reference surface forming interference fringes (measured by an photovoltaic detector) allowing precise depth-resolved imaging of the plaque on a micron scale.

OCT uses narrow linewidth tunable laser source or a superluminescent diode source emitting light over a broad bandwidth (distribution of wave length) to make in situ tomographic images with axial resolution of 10-20 µm and tissue penetration of 2-3 mm. OCT has the potential to image tissues at the level of a single cell. In fact, the inventors have recently utilized broader band width optical sources such as femtosecond pulsed lasers, so that axial resolution is improved to 4 microns or less. With such resolution, OCT can be applied to visualize intimal caps, their thickness, and details of structure including fissures, the size and extent of the underlying lipid pool and the presence of inflammatory cells. Moreover, near infrared light sources used in OCT instrumentation can penetrate into heavily calcified tissue regions characteristic of advanced coronary artery disease. With cellular resolution, application of OCT may be used to identify other details of the vulnerable plaque such as infiltration of monocytes and macrophages. In short, application of OCT can provide detailed images of a pathologic specimen without cutting or disturbing the tissue.

One concern regarding application of this technology to image atherosclerotic plaques within the arterial lumen is the strong scattering of light due to the presence of red blood cells. Once a catheter system is positioned in a coronary artery, the blood flow between the OCT optical fiber and artery can obscure light penetration into the vessel wall. One proposed solution is the use of saline flushes. Saline use is limited in duration, however, since myocardial ischemia eventually occurs in the distal myocardium. The inventors have proposed the use of artificial hemoglobin in the place of saline. Artificial hemoglobin is non-particulate and therefore does not scatter light. Moreover, artificial hemoglobin is about to be approved by the United States Food and Drug Administration as a blood substitute and can carry oxygen necessary to prevent myocardial ischemia. Recently, the inventors demonstrated the viability of using artificial hemoglobin to reduce light scattering by blood in mouse myocardium coronary arteries (Villard J W, Feldman M D, Kim Jeehyun, Milner T E, Freeman G L. Use of a blood substitute to determine instantaneous murine right ventricular thickening with optical coherence tomography. *Circulation* 2002; Volume 105: Pages 1843-1849, incorporated by reference herein).

The first prototype of an OCT catheter to image coronary plaques has been built and is currently being tested by investigators in Boston at Harvard-MIT (Jang I K, Bouma B E, Kang D H, et al. Visualization of coronary atherosclerotic plaques in patients using optical coherence tomography: comparison with intravascular ultrasound. *JACC* 2002; 39: 604-609, incorporated by reference herein) in association with Light Lab Co. The prototype catheter consists of a single light source and is able to image over a 360 degree arc of a coronary arterial lumen by rotating a shaft that spins the optical fiber. Because the rotating shaft is housed outside of the body, the spinning rod in the catheter must rotate with uniform angular velocity so that the light can be focused for equal intervals of time on each angular segment of the coronary artery. Mechanical drag in the rotating shaft can produce significant distortion and artifacts in recorded OCT images of the coronary artery. Unfortunately, because the catheter will always be forced to make several bends between the entry point in the femoral artery to the coronary artery (e.g., the 180 degree turn around the aortic arch), uneven mechanical drag will result in OCT image artifacts. As the application of OCT is shifted from imaging gross anatomical structures of the coronary artery to its capability to image at the level of a single cell, non-uniform rotation of the single fiber OCT prototype will become an increasingly problematic source of distortion and image artifact.

Essentially, current endoscope type single channel OCT systems developed by Light Lab Co. suffers by non-constant rotating speed that forms irregular images of a vessel target. See U.S. Pat. No. 6,134,003, incorporated by reference herein. Their approach of a rotary shaft to spin a single mode fiber is prone to produce artifact. The catheter will always be forced to make several bends from its entry in the femoral artery, to the 180 degree turn around the aortic arch, to its final destination in the coronary artery. All these bends will cause uneven friction on the rotary shaft, and uneven time distribution of the light on the entire 360 degree arch of the coronary artery. As the application of OCT is shifted from gross anatomical structures of the coronary artery to its capability to image at the level of a single cell, then non-uniform rotation of the single fiber OCT will become even a greater source of greater artifact.

The present invention solves rotational distortion and related artifactual problems by developing a multiphase array OCT catheter. By incorporating 10-60 individual OCT fibers within a single catheter, rotation of the optical fiber or similar element (e.g., micro-motor driven mirror) and associated image distortion and artifacts are eliminated and spatial resolution may be improved. The catheter will allow 10-60 individual sources of light to independently image the 360 degree arc of the coronary arterial lumen. An additional advantage of the multiphase array is provision of greater spatial resolution of the object being interrogated in comparison to single fiber designs. Many investigators recognize that a single rotating fiber or micro-motor driven mirrors utilized in current designs will not allow imaging at the level of a single cell while the multiphase array approach can provide cellular resolution.

The construction of a multiphase array OCT catheter requires resolution of a number of problems using innovative design solutions. Successful design and demonstration of the catheter requires the development of an optical channel containing 10-60 individual fibers in a 1.5 mm diameter. Each fiber requires a lens to focus the light, and a mirror fabricated using nanotechnology to redirect light from each fiber by 90 degrees from the catheter to the luminal surface of the coronary artery. Further, each of the 10-60 light paths has to be split again for both reference and artery paths. The present invention provides design solutions to both the catheter and multichannel interferometer.

SUMMARY OF THE INVENTION

The present invention pertains to an endoscope for a patient. The endoscope comprises a light producing means, such as a light source. The endoscope comprises an optical fiber array comprising a plurality of optical fibers adapted to be disposed in the patient. The optical fiber array transmits the light from the light producing means into the patient, and transmits the light reflected by the patient out of the patient. The plurality of the optical fibers of the array in optical communication with the light producing means. The endoscope comprises a detector for receiving the light from the array and analyzing the light. The plurality of the optical fibers of the array in optical communication with the detector.

The present invention pertains to a method for imaging a patient. The method comprises the steps of transmitting light from a light source into an optical fiber array comprising a plurality of optical fibers in the patient. There is the step of transmitting the light reflected by the patient out of the patient. There is the step of receiving the light from the array at a detector. There is the step of analyzing the light with the detector.

The present invention pertains to an apparatus for studying an object. The apparatus comprises means for producing light. The apparatus comprises means for analyzing the light that has reflected from the object based on polarization, space, position or angle.

The present invention pertains to an apparatus for studying an object. The apparatus comprises means for producing light. The apparatus comprises means for analyzing the light that has reflected from the object based on polarization.

The present invention pertains to an apparatus for studying an object. The apparatus comprises means for producing light. The apparatus comprises means for analyzing the light that has reflected from the object based on space.

The present invention pertains to an apparatus for studying an object. The apparatus comprises means for producing light. The apparatus comprises means for analyzing the light that has reflected from the object based on angle.

The present invention pertains to a method for studying an object. The method comprises the steps of producing light. The method comprises the steps of analyzing the light that has reflected from the object based on polarization, space, position or angle.

The present invention pertains to a method for studying an object. The method comprises the steps of producing light. The method comprises the steps of analyzing the light that has reflected from the object based on polarization.

The present invention pertains to a method for studying an object. The method comprises the steps of producing light. The method comprises the steps of analyzing the light that has reflected from the object based on space.

The present invention pertains to a method for studying an object. The method comprises the steps of producing light. The method comprises the steps of analyzing the light that has reflected from the object based on angle.

BRIEF DESCRIPTION OF THE DRAWINGS

In the accompanying drawings, the preferred embodiment of the invention and preferred methods of practicing the invention are illustrated in which:

FIG. 5 is a schematic representation of a side view of the sample arm.

FIG. 6 is a schematic representation of an axial view of the sample arm.

FIG. 7 is a schematic representation of a top view of an axicon lens.

FIG. 8 is a schematic representation of an optical fiber array of the sample arm.

FIG. 9 is a schematic representation of a perspective view of a probe tip of the sample arm emphasing the mirrors to refocus the light on the tissue of interest.

FIG. 10 is a schematic representation of a side view of a groove of the tip with an attached fiber ending with a 45° angled mirror (reflection).

FIG. 11 is a schematic representation of a top view of the tip with an attached fiber.

FIGS. 18a and 18b are schematic representations of an hydraulic mechanism.

DETAILED DESCRIPTION

Figure 1:
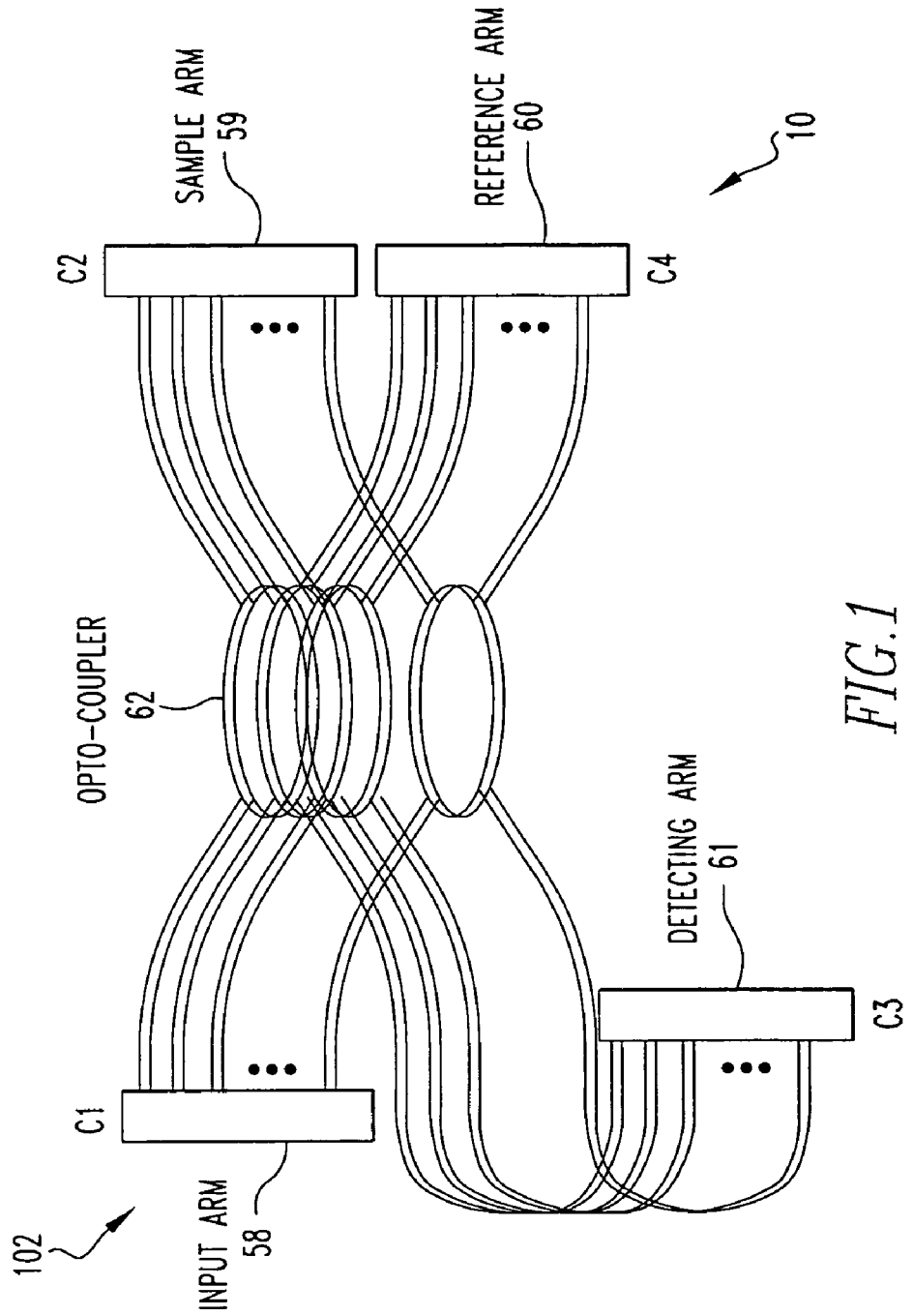
FIG. 1 is a schematic representation of an overview of the present invention.

Referring now to the drawings wherein like reference numerals refer to similar or identical parts throughout the several views, and more specifically to FIGS. 1-5, 15 and 16 thereof, there is shown an endoscope 10 for a patient. The endoscope 10 comprises means 102 for producing light, such as a light source 51. The endoscope 10 comprises an optical fiber array 28 comprising a plurality of optical fibers 8 adapted to be disposed in the patient. The optical fiber array 28 transmits the light from the producing means, preferably including a light source 51, into the patient, and transmits the light reflected by the patient out of the patient. The plurality of the optical fibers 8 of the array 28 is in optical communication with the light producing means 102. The endoscope 10 comprises a detector D for receiving the light from the array 28 and analyzing the light. The plurality of the optical fibers 8 of the array 28 is in optical communication with the detector D.

Preferably, the endoscope 10 includes a tube 53 about which the plurality of optical fibers 8 are disposed. The tube 53 preferably has grooves 54 that extend longitudinally along the tube 53, as shown in FIG. 10. One of the plurality of optical fibers 8 is disposed in each of the grooves 54. Preferably, the endoscope 10 includes a probe tip 55, as shown in FIG. 11, having a reflector 56 disposed in each groove which reflects light from the optical fiber 8 in the groove when the reflector 56 is in the patient and reflects light from the patient to the optical fiber 8 when the array 28 is in the patient.

Figure 12:
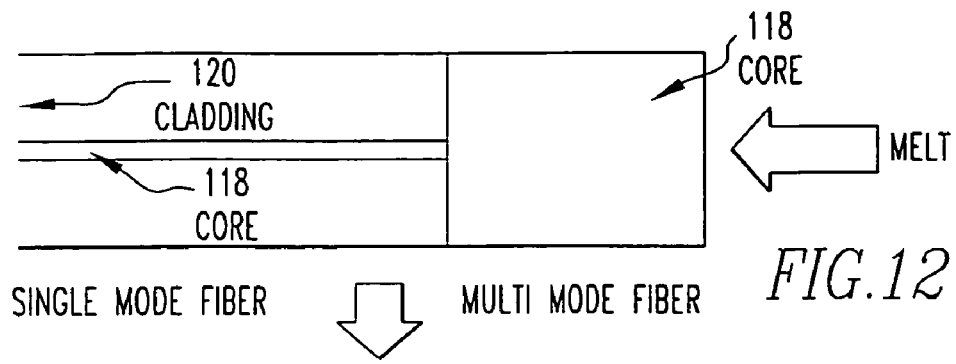
FIG. 12 is a schematic representation of a first step of manufacture of each fiber lens of the sample arm.
Figure 13:
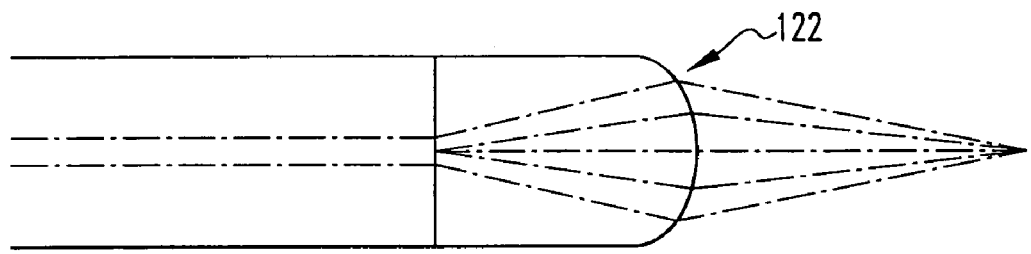
FIG. 13 is a schematic representation of a second step in the manufacture of each fiber lens of the sample arm.

The light source 51 preferably includes a coherent light source 51 and means 57 for guiding the light from the light source 51 to the plurality of optical fibers 8 of the array 28. Preferably, the optical fiber 8 is single mode, has a core 118 with cladding 120 disposed about the core 118, and has a lens 122 at its tip which focuses the light from the core 118 to the reflector 56 and light from the reflector 56 to the core 118, as shown in FIGS. 12 and 13. The array 28 preferably includes a transparent cover 7.

Preferably, the light source 51 comprises an input arm 58, the array 28 comprises a sample arm 59, the detector D comprises a reference arm 60 and a detector arm 61; and the input arm 58, the detector arm 61, the sample arm 59 and the reference arm 60 together form an interferometer. The reference arm 60 preferably uses RSOD to introduce depth scanning and dispersion compensation to the interferometer.

Preferably, the endoscope 10 includes an opto-coupler 62 which optically couples corresponding optical fibers 8 of the input arm 58, sample arm 59, reference arm 60 and detecting arm together. The detector D preferably determines structural information about the patient from the intensity of an interference signal from reflected light from corresponding fibers of the sample arm 59 and the reference arm 60 having a same bypass length.

Preferably, the probe tip 55 includes a scanning head 1 which holds N optical fibers 8, where N is greater than or equal to 2 and is an integer, as shown in FIGS. 17-22c. The N optical fibers 8 are preferably arranged around the scanning head 1 in parallel and equal spacing. Preferably, the probe tip 55 includes a mechanism 134 for moving the scanning head 1 so each of the optical fibers 8 scan an angular range of N/360 degrees. The moving mechanism 134 preferably includes a mechanism 9 for linear motion which causes the scanning head 1 to rotate.

Preferably, the linear motion mechanism 9 includes a fiber shaft holder having a shaft channel 31 extending axially along the holder, and N fiber channels 32 are arranged around the holder in parallel with the shaft channel 31, and a twisting shaft that fits in and conforms with the shaft channel 31, as the shaft moves in the channel, the holder rotates.

The scanning head 1 preferably has a socket head that conforms with the shaft and causes the scanning head 1 to rotate. Preferably, the probe tip 55 includes a guide wire holder 2 disposed on the scanning probe 50 which receives and follows a guide wire when the guard wire is in a blood vessel, biliary tract, and possible GU tract. A guide wire is not necessary in the GI tract. Preferably, the endoscope 10 includes a spring disposed between the scanning head 1 and the fiber shaft holder which forces the shaft back after the shaft has moved forward.

The present invention pertains to a method for imaging a vessel, GU, GI or biliary tract of a patient. The method comprises the steps of transmitting light from a light source 51 into an optical fiber array 28 comprising a plurality of optical fibers 8 in the patient. There is the step of transmitting the light reflected by the patient out of the patient. There is the step of receiving the light from the array 28 at a detector D. There is the step of analyzing the light with the detector D.

Preferably, there are the steps of reflecting light from each optical fiber 8 with a corresponding reflector 56 associated with the fiber, and reflecting light from the patient to the associated fiber with a reflector 56. There is preferably the step of moving each of N optical fibers 8 comprising the optical fiber array 28 an angular range of N/360 degrees. Preferably, there is the step of applying a linear motion to cause each of the N optical fibers 8 of the optical fiber array 28 to move the angular range.

The step of applying the linear motion preferably includes the step of moving axially forward in parallel with the N optical fibers 8 a twisting shaft through a shaft channel 31 extending axially along a fiber shaft holder having N fiber channels 32 arranged around the holder in parallel with the shaft channel 31 which causes the holder to rotate. Each of the N optical fibers 8 is disposed in a respective fiber channel 32 of the N fiber channels 32. The twisting shaft fits in and conforms with the shaft channel 31, as the shaft moves in the channel. Preferably, there is the step of guiding the optical fiber array 28 along a guide wire which is received by a guide wire holder 2 when the guide wire is in a blood vessel, biliary tract, and possibly GU system, but not in the GI tract.

The present invention pertains to an apparatus for studying an object. The apparatus comprises means for producing light. The apparatus comprises means for analyzing the light that has reflected from the object based on polarization, space, position or angle.

Figure 31:
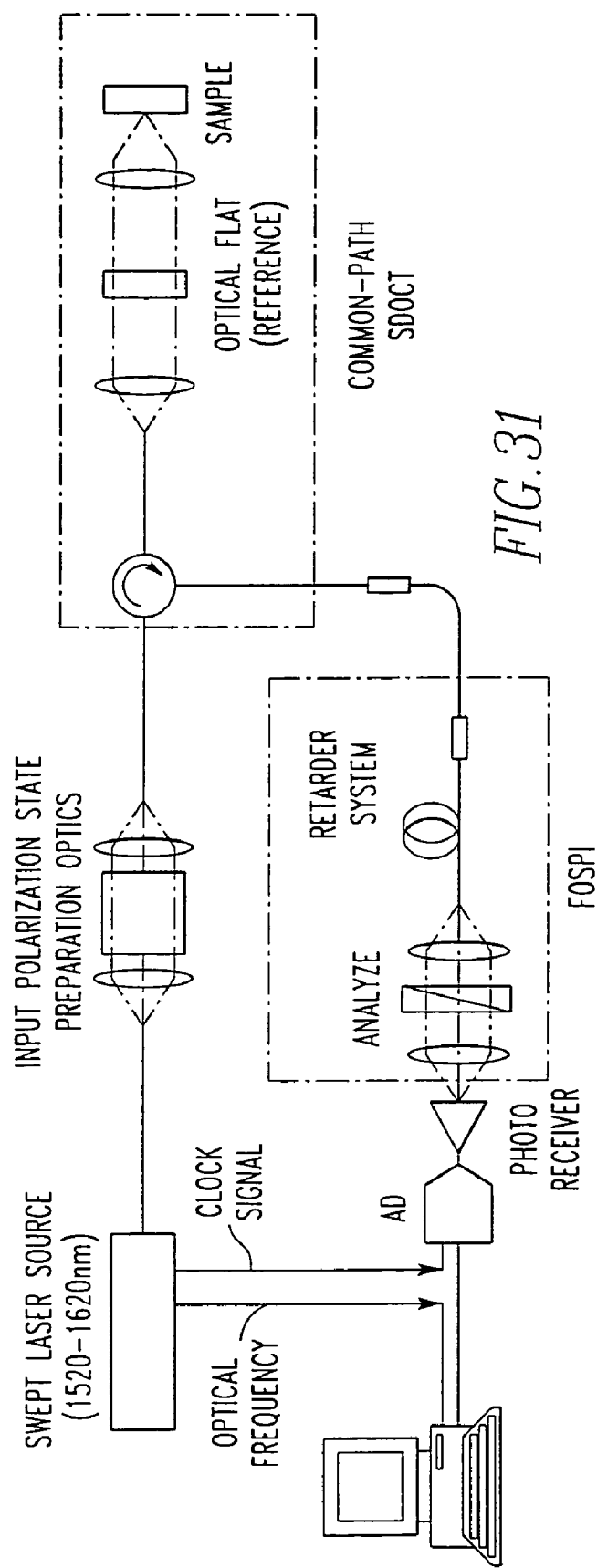
FIG. 31 is a schematic diagram of single channel fiber-based polarization sensitive spectral domain optical coherence tomography with a fiber optic spectral polarimetry instrument (FOSPI).
Figure 32:
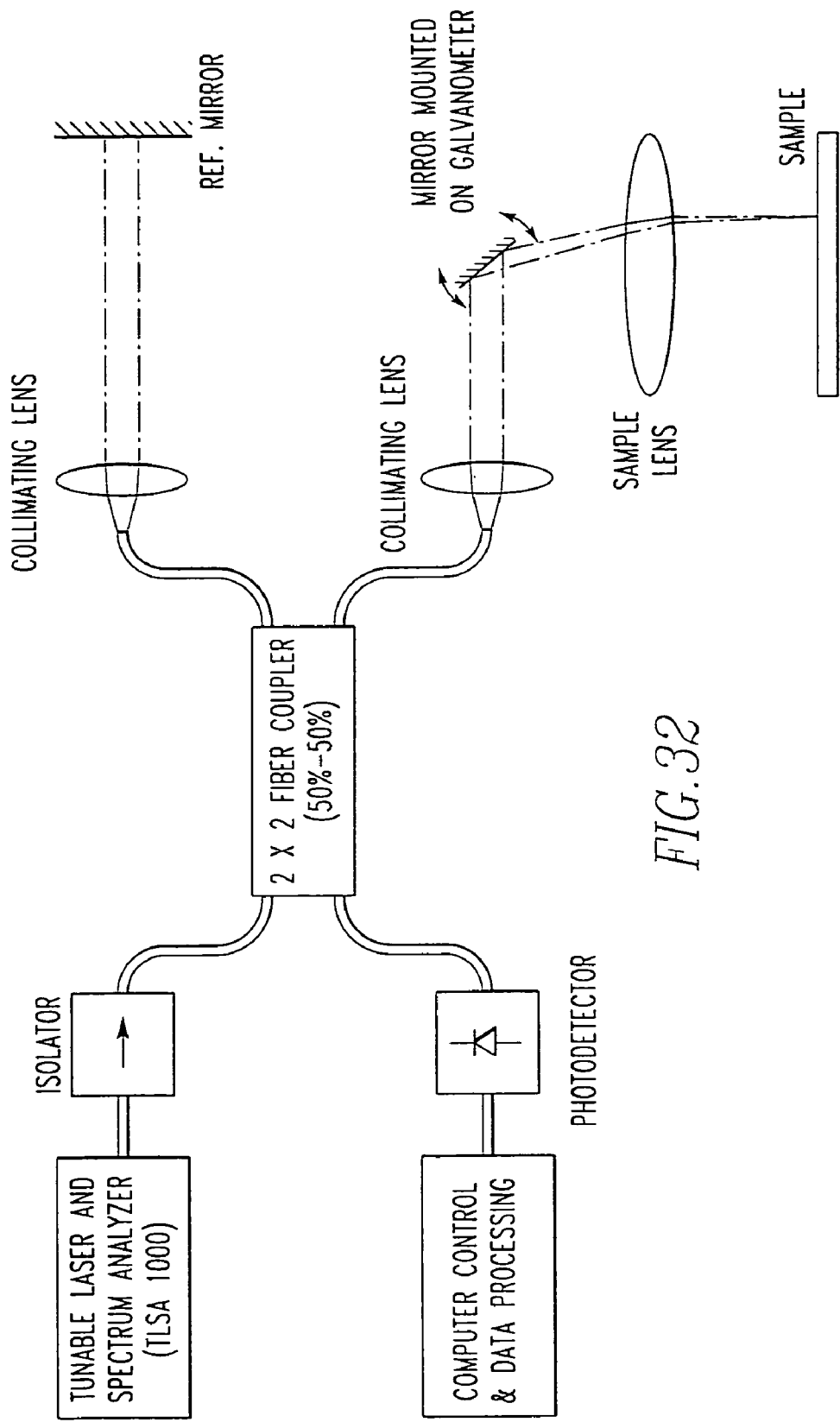
FIG. 32 is a schematic representation of a fiber-based spatially multiplexed swept source optical coherence tomography.
Figure 33:
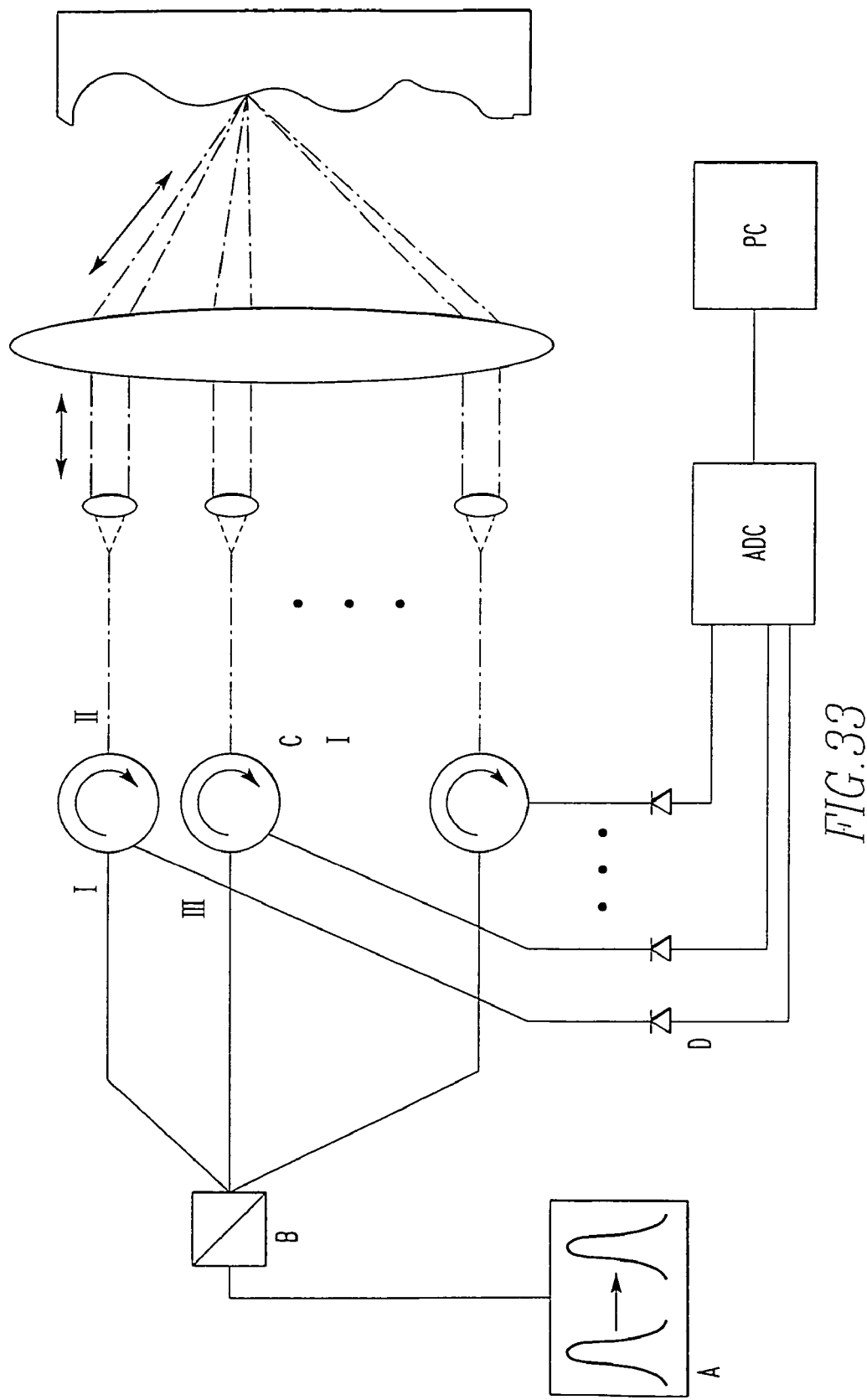
FIG. 33 is a schematic representation of a multi-fiber angle-domain OCT.

The means for analyzing is preferably described in the figures, where polarization is found in FIG. 31, position in FIGS. 1-30, space in FIG. 32, and angle in FIG. 33.

The present invention pertains to an apparatus for studying an object. The apparatus comprises means for producing light. The apparatus comprises means for analyzing the light that has reflected from the object based on polarization.

The present invention pertains to an apparatus for studying an object. The apparatus comprises means for producing light. The apparatus comprises means for analyzing the light that has reflected from the object based on space.

The present invention pertains to an apparatus for studying an object. The apparatus comprises means for producing light. The apparatus comprises means for analyzing the light that has reflected from the object based on angle.

The present invention pertains to a method for studying an object. The method comprises the steps of producing light. The method comprises the steps of analyzing the light that has reflected from the object based on polarization, space, position or angle.

The present invention pertains to a method for studying an object. The method comprises the steps of producing light. The method comprises the steps of analyzing the light that has reflected from the object based on polarization.

The present invention pertains to a method for studying an object. The method comprises the steps of producing light. The method comprises the steps of analyzing the light that has reflected from the object based on space.

The present invention pertains to a method for studying an object. The method comprises the steps of producing light. The method comprises the steps of analyzing the light that has reflected from the object based on angle.

In the operation of the invention, a near infrared broadband light source 51 sends a light beam into the input arm 58 of the array 28 type interferometer. The beam profile from the light source 51 is a circular gaussion. The optics before connector 1 makes the beam profile linear and focuses it into the connector 1. The array 28 type interferometer consists of multiple fiber-based interferometer that has four fiber arms connected to an opto-coupler 62. Incoming light into the input arm 58 is divided to the sample and reference arms 59, 60, respectively. In the sample arm 59, optical fibers 8 are distributed like an annular ring, and light will be focused at the target vessel perpendicular to the optical axis. In the reference arm 60, RSOD introduces depth scanning and dispersion compensation. When the reflected light from both arms have the same light path length, strictly speaking within a coherence length, interference occurs. The intensity of the interference signal represents the structural information of a sample.

Figure 2:
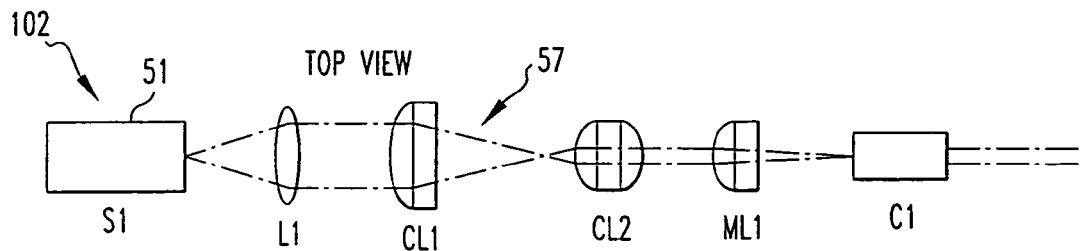
FIG. 2 is a top view of an input arm (light source) of the present invention.
Figure 3:
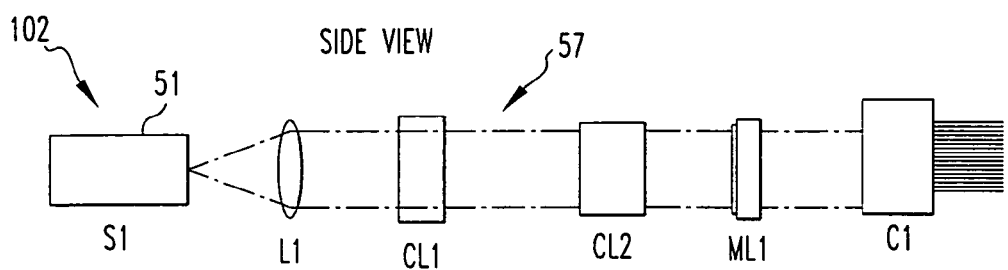
FIG. 3 is a schematic representation of a side view of the input arm (light source).

More specifically, in regard to the input arm 58, and referring to FIGS. 1, 2 and 3, a single beam comes out of S1 and will be collimated by L1. At this point, the beam diameter is big enough to project across all of C1's area, but the beam is still circular. CL1 and CL2, circular lenses, change the beam profile to a linear shape, which means that the beam is not circular anymore, but it looks narrow from FIG. 2 and the same shape with the beam after L1 on FIG. 3. ML1 focuses all light onto C1.

This is known as an open optic solution:
- Light source S1 has a fiber tip from which light departs into air.
- L1 is a collimating lens 122, so the fiber tip of the light source 51 should be located at the back of the focal point of L1 in order to collimate the light.
- CL1, 2 are cylindrical lenses. Separation between two is the sum of each cylindrical lens 122 focal length. They work as a telescope which decrease beam size only in one direction. In other words, the size of the beam does not change from FIG. 3.
- ML1 is a micro lens array 28, which has a lot of small lenses. Each of the small lenses is positioned to have a focal point at each fiber entrance of C1. C1 should be located at the focal point of ML1. All micro lenses have same focal length. C1 is a linear fiber array 28.

Figure 4:
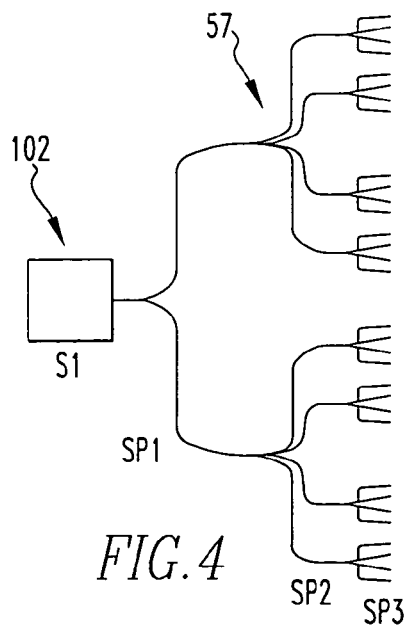
FIG. 4 is a schematic representation of a fiber based solution for the input arm.

In an alternative embodiment of the input arm 58, as shown in FIG. 4, known as a fiber based solution:
- Light source S1 is connected to a single mode fiber, which is connected to fiber splitter (50:50), S1.
- The first fiber splitter is 1 by 2. Each output end of the 1*2 fiber splitter is connected to 1*4 splitter, SP1.
- Each output end of the 1*4 splitter, $2^{nd}$ layer, is connected to another 1*4 splitter, $3^{rd}$ layer, SP2.
- At the output of the $3^{rd}$ layer, the number of fiber is 32. 32 fiber comprises a linear fiber array 28, SP3.

Linear fiber array 28:
- Each fiber is a single mode fiber, which can have a different cutoff frequency. The cutoff frequency is dependent on the center wavelength of the light source 51. Usually, 850 nm or 1300 nm of center wavelength for the light source 51 are used.
- Each fiber is attached to another so that all together they form a linear fiber array 28.

C1 is connected to multiple interferometers. Each interferometer consists of four fiber arms and opto-coupler 62. At each end of each arm, there is a linear array 28 fiber connector (C1, C2, C3 C4). Incoming light will be divided by the opto-coupler 62 into the sample and reference arms 59, 60, respectively.

With respect to the sample arm 59, this sample arm 59, as shown in FIGS. 5, 6, 7, 8 and 17, goes into the target vessel. C2 is connected to a linear fiber array 28 which is of an annular shape at the other end. The total length of the arm will be around 2~3 m. When the light leaves the annular tip F, it will be collimated by L1 and then reflected by L2 outward from the probe.

Reflected light from tissue will follow back to L2 and L1 and be gathered by the fiber tip. Later, two reflected lights from the sample and reference arms 59, 60, respectively, will make interference, which will be detected by the array 28 detector D at the detection arm.

The sample arm 59 is supposed to go through a target vessel, GI, GU or biliary tract. C2 is connected to a linear fiber array 28 which has an annular shape at the other end (probe tip 55) (FIG. 8). Total length of the sample arm 59 is about 1.5 m. The fiber array 28 will be molded by a transparent cover 7 material (ex: silicon resin or polymers).

At the annular probe tip F shown in FIG. 9, each fiber is glued at a groove of a cylindrical polymer tube 53. The shape of each groove is shown at FIGS. 10 and 11. Each groove end has a reflector 56 which is 45° oblique to axial direction. The groove will be made by micro fabrication technique. Each fiber has a lens 122 at the tip, which can be manufactured by splicing a multimode fiber with the same diameter of the cladding 120 of the single mode fiber and then melting the end of multimode fiber in order to get curvature (FIGS. 12 and 13). When the light leaves the fiber tip, the light will be reflected outward by the reflector 56 at the end of the groove, and then will be focused at the target tissue area. Reflected light from the tissue will follow back the same path as the incoming light, and go to the detection arm.

Micromachining or micro-electro-mechanical systems (MEMS) and nanotechnology are becoming increasingly popular for the development of improved biomaterials and devices (Macilwain C., "US plans large funding boost to support nanotechnology boom," *Nature*, 1999; 400:95, incorporated by reference herein). Similar to manufacturing methods used for computer microchips, MEMS processes combine etching and/or material deposition and photolithographic-patterning techniques to develop ultrasmall devices (Madou, M., "Fundamentals of microfabrication," *CRC Press: Boca Raton*, 2002, incorporated by reference herein). MEMS has been proven promising in medicine for its small mass and volume, low cost, and high functionality. Successful MEMS devices in medicine include smart sensor for cataract removal, silicon neurowells, microneedles for gene and drug delivery, and DNA arrays (Polla, D. L., Erdman, A. G., Robbins, W. P., Markus, D. T., Diaz-Diaz, J., Rizq, R., Nam, Y., Brickner, H. T., Wang, A., Krulevitch, P., "Microdevices in Medicine," *Annu. Rev. Biomed. Eng.*, 2000; 02:551-76; McAllister et al., 2000, both of which are incorporated by reference herein). However, most of the MEMS processes are planar in nature for two-dimension (2D) microfeatures and primary for processing silicon material. Other micromachining processes include laser beam micromachining (LBM), micro-electrical discharge machine (micro-EDM), and electron beam machining (EBM) (Madou, M., "Fundamentals of microfabrication," *CRC Press: Boca Raton*, 2002), incorporated by reference herein. Micro-fabrication and micro-device development using metals, metal alloys, silicon, glass, and polymers are described in the following. (Chen, S. C., Cahill, D. G., and Grigoropoulos, C. P., "Transient Melting and Deformation in Pulsed Laser Surface Micro-modification of Ni—P Disks," *J. Heat Transfer*, vol. 122 (no. 1), pp. 107-12, 2000; Kancharla, V. and Chen, S. C., "Fabrication of Biodegradable Microdevices by Laser Micro-machining of Biodegradable Polymers," *Biomedical Microdevices*, 2002, Vol. 4(2): 105-109; Chen, S. C., Kancharla, V., and Lu, Y., "Laser-based Microscale Patterning of Biodegradable Polymers for Biomedical Applications," in press, *International J. Nano Technology*, 2002; Zheng, W. and Chen, S. C., "Continuous Flow, nano-liter Scale Polymerase Chain Reaction System," *Transactions of NAMRC/SME*, Vol. 30, pp. 551-555, 2002; Chen, S. C., "Design and Analysis of a Heat Conduction-based, Continuous Flow, Nano-liter Scale Polymerase Chain Reaction System," *BECON*, 2002, all of which are incorporated by reference herein).

For the array 28, a stainless steel cylinder is chosen with a diameter of 1.5 mm as the base material. The diameter is 1.0 mmm for vascular applications, larger for GU, GI and biliary applications, up to 3.0 mm, if desired. Both the micro-grooves 54 (or micro-channels of 200 microns wide) and the reflecting surfaces are machined by micro-electrical discharge machining (micro-EDM) or micro-milling using focused ion machined tool. To enhance the reflectivity of the reflecting surface, the stainless steel cylinder are coated with evaporated aluminum using electron-beam evaporation.

Figure 14:
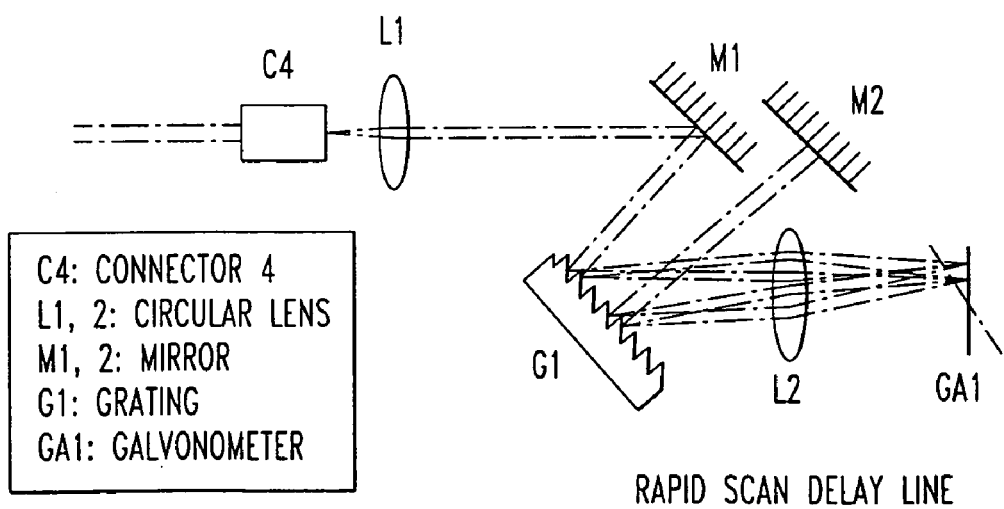
FIG. 14 is a schematic representation of a reference arm of the present invention.

In regard to the reference arm 60, shown in FIG. 14, light is collimated by L1 after leaving connector C4, and be spectrally distributed by a grating (G1) and will be focused to a mirror (GA1). By vibrating GA1, the light path length will be changed in order to achieve depth scanning.

There are many options to build the reference arm 60 applying existing techniques. A very simple form of the reference arm 60 has just a mirror attached onto a voice coil that is driven by a function generator with sine wave. The light reflects back by the mirror and the mirror position changes the light path length. This path length change provides depth scanning of the target tissue because interference occurs only when both arms have the same light path length. Preferably, the reference arm 60 is more complicated than the simple one. That is called Rapid-Scanning Optical Delay (RSOD) which can provide fast depth scanning and dispersion compensation.

Linear array type beam launches from C4, and is collimated by L1. A mirror (M1) reflects the beam to a grating (G1) which spectrally distributes the broadband source light. Spectrally distributed light will be focused on a Galvono-scanning mirror (GA1) by a lens (L2). Separation between G1 and L2 determines the amount of chromatic dispersion degree so any material dispersion can be compensated for usually caused by fibers. The beam offset from the scanning mirror center determines the fringe frequency that will show up after interfering two reflected lights. The reflected light from the GA1 goes to L2, G1, and to M2. And then the light reflected following back incoming path and will be coupled back to C4.

Figure 15:
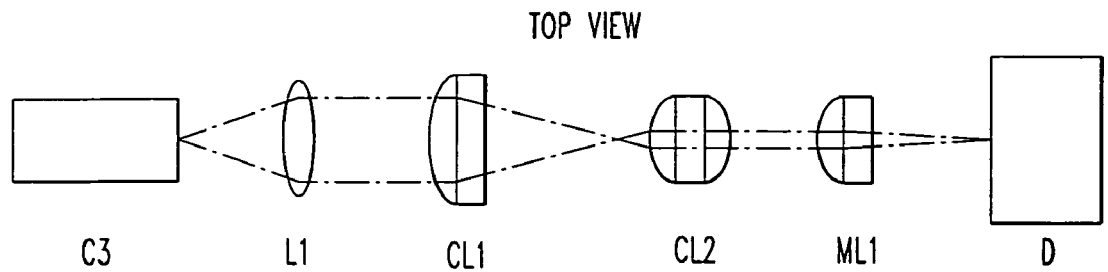
FIG. 15 is a schematic representation of a top view of a detection arm of the present invention.
Figure 16:
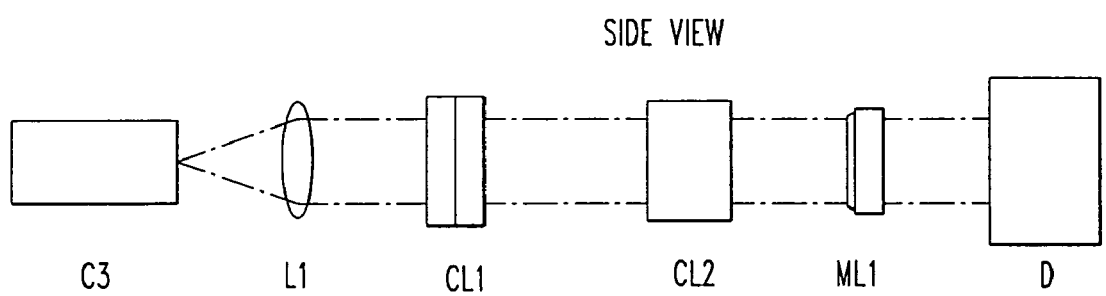
FIG. 16 is a schematic representation of a side view of the detection arm.

Referring to the detection arm, as shown in FIGS. 15 and 16, light is collimated by L1 after leaving connector C3, and is circular. Combination of CL1 and CL2 makes the beam look linear in one plane (horizontal). Micro-lens array ML1 makes the light focus on the array 28 detector D.

Figure 17A:
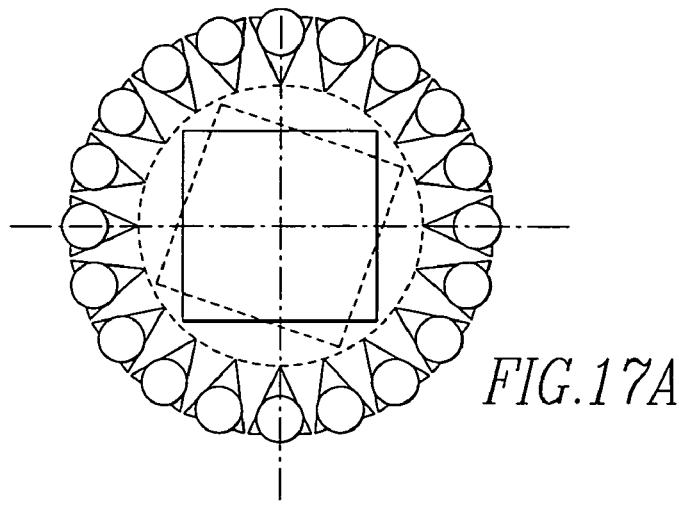
FIG. 17 is an alternative schematic representation of a scanning probe of the sample arm.
Figure 17:
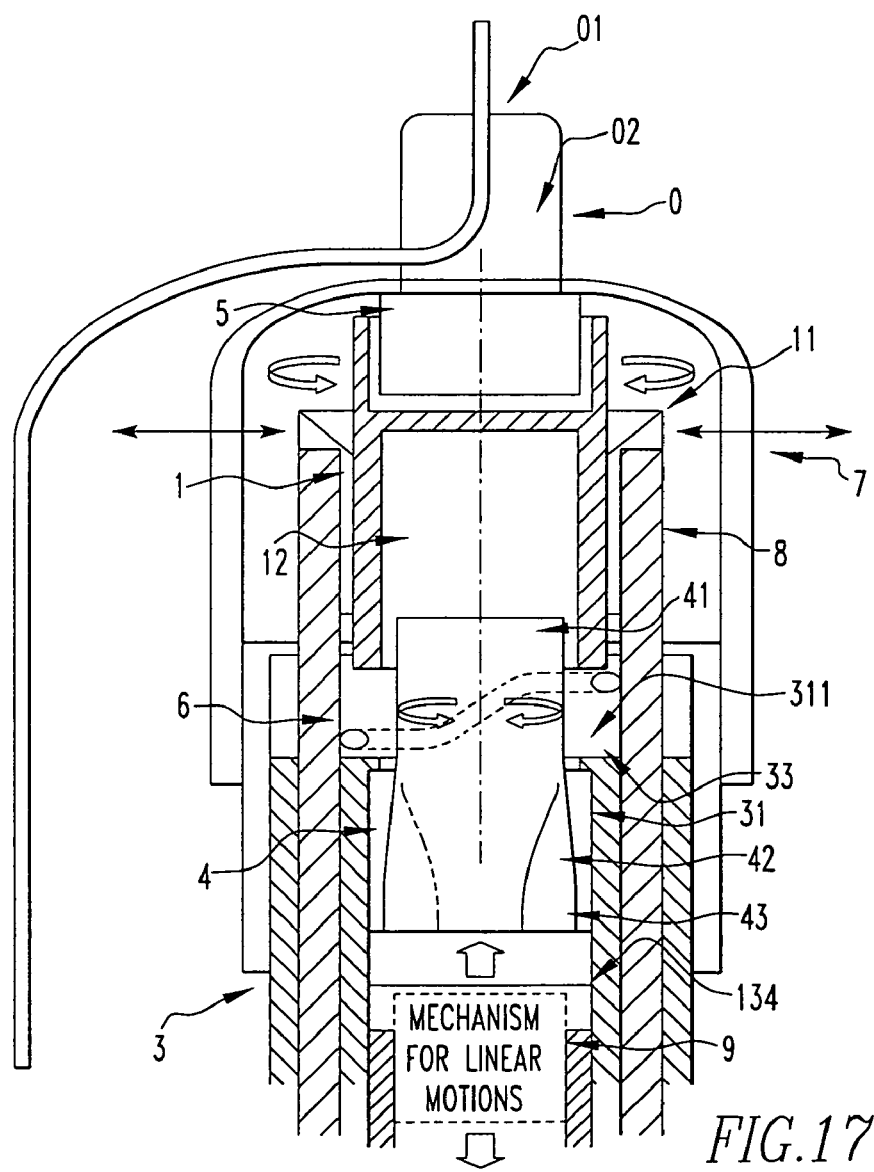
Figure 19A:
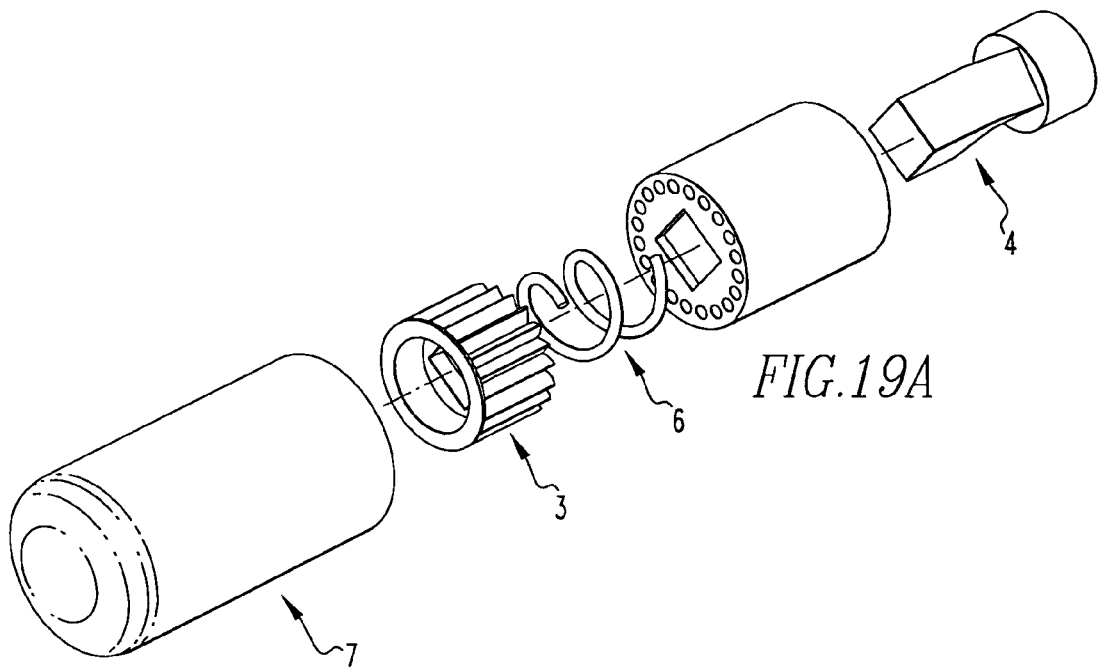
FIGS. 19a and 19b are schematic representations of exploded views of the hydraulic mechanism.
Figure 19B:
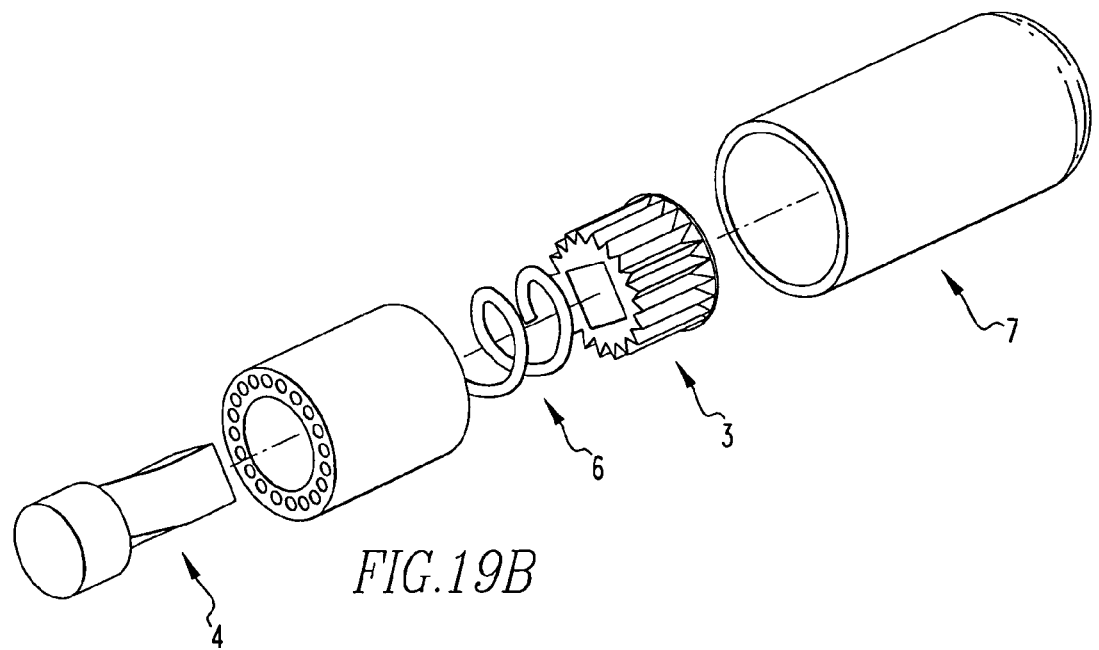

As shown in FIGS. 17, 19a, and 19b, the scanning probe 50 is comprised of a scanning head 1, a fiber-shaft holder 3, a twisted shaft 4, a transparent cover 7, a guide wire holder 2, and a mechanism 9 for linear motion. In this embodiment, the scanning head 1 is adapted to hold a fiber bunch that contain 20 optical fibers 8, which are arranged around the scanning head 1 in parallel and equal spacing. In operation, each of the fibers is set to scan an angular range of 18 degrees ($360°÷20=18°$). Reflective surfaces 11 are formed on the scanning head 1 and are oriented 45° degrees to the central axis of each respective optical fibers 8, such that they would guide the light from the fiber bunch and direct the light through the transparent cover 7.

The scanning head 1 is designed to provide an 18 degrees' back-and-forth rotation. The back-and-forth rotation realizes the scanning function required by the OCT system. The mechanism of this back and forth rotation is described below.

The fiber-shaft holder is substantially a multi-tubular structure. It is formed with one shaft channel 31 extending along the central axis of the fiber-shaft holder and 20 fiber channels 32 arranged around the fiber-shaft holder 3 in parallel. The optical fibers 8 extend through respective fiber channels 32. The shaft channel 31 has a round cross-sectional area. At the upper end of the shaft channel 31, the shaft channel 31 is an opening, but the geometry of the opening is reduced from the round cross-sectional area to a rectangular cross-sectional hole 311. The reason for this structural design will be described along with the description of the twisted shaft 4.

The twisted shaft 4 has a rectangular cross-section area, which is identical in geometry to the rectangular cross-sectional hole of the fiber-shaft holder 3. Indicated by its name, the shaft 4 is partially twisted along the shaft central axis and can be divided into a non-twisted part 41 and a twisted part 42. In assembly, the shaft 4 is passed through the rectangular cross-sectional hole of the fiber-shaft holder 3, and it is enabled to slide back-and-forth via the rectangular cross-sectional hole. The relative motion of the surfaces of the rectangular cross-sectional hole and the twisted shaft 4 form the mechanism that realizes a back-and-forth rotation. The reason is that when the twisted part 42 of the shaft 4 slides through the rectangular cross-sectional hole, the shaft 4 itself is forced to rotate along the shaft central axis to fit the matching of both the surfaces of the rectangular cross-sectional hole and the twisted shaft 4. Particularly, the shaft 4 and the holder 3 compose a mechanism 9 that can transmit a linear motion into a rotational motion.

The description is now focused on the scanning head 1. The scanning head 1 has a rectangular socket 12, which has a cross-section area identical to that of the twisted shaft 4. The rectangular socket 12 provides a channel covering the non-twisted part 41 of the twisted shaft 4 and lets the non-twisted part 41 exert the back-and forth motion inside the rectangular socket 12. The moving range of the shaft 4 is constrained such that the twisted part 42 does not pass into the scanning head's rectangular socket 12 (that will result in a geometric mismatch), but the twisted part 42 only interacts with the fiber-shaft holder's rectangular cross-sectional hole. According to the description above, the motion of the shaft 4 is comprised of a linear component (V) and an angular component ($\omega$). Referring to the geometry of the rectangular socket 12 and non-twisted part 41 of the shaft 4, the shaft motion's linear component (V) would not contribute to the motion of the scanning head 1 (regardless of the friction between the surfaces), but the angular component ($\omega$) does. The scanning head 1 rotates back and forth with the rotational motion of the twisted shaft 4, which in turn results from the twisted shaft's linear back-and-forth movement relative to the fiber-shaft holder 3. As a result, the scanning head 1 provides a back-and-forth rotational motion transmitted from the back and forth linear motion provided by the twisted shaft 4.

A guide wire holder 2 is a module used to guide the scanning probe 50 toward the investigated section of the detected blood vessel, biliary duct, and possibly GU application. For the GI tract, a guide wire is generally not used. In operation, a guide wire 01, or "guide tissue", is previously disposed along a specific route of human vessels, such that a track for the scanning probe 50 of the OCT system can be formed. The guide wire holder 2 constrains the scanning probe 50 such that it can only slide along the track formed by the guide wire 01. The scanning probe 50 is therefore guided to the patient section to be investigated.

Guide wire holder 2 and holder 5 function as bearings of the scanning head 1. They constrain the movement of the scanning head 1 and stabilize it. As well, a compressive spring 6 is disposed between the scanning head 1 and the fiber-shaft holder 3. The spring 6 is mildly compressed in assembly, such that it pushes the scanning head 1 against the holder 5 and eliminates any potential axial movement of the scanning head 1 that may result in axial positioning errors ($\Delta d$). It is preferable that the spring 6 supplies torque between the scanning head 1 and the fiber-shaft holder 3. The spring 6 has its both ends, respectively, fixed on the scanning head 1 and the fiber-shaft holder 3. The spring 6 is mildly twisted in assembly. By this means, the spring can provide a torque to the back-and-forth rotational mechanism, such that the backlash (resulting from, for example, the tolerance between the rectangular cross-sectional hole and the shaft) of the rotational mechanism, as well as the resultant angular positioning errors ($\Delta\theta$), are eliminated.

Note that, the cross-section geometry of the shaft channel 31 is circular. With respect to the shaft channel 31, the twisted shaft 4 is formed with a cylinder part 43 at its end of the twisted part 42. The cylinder part 43 and the shaft channel 31 performs a motion like a piston. In an upward movement of the twisted shaft 4, due to the geometric difference, the cylinder part 43 would be blocked at the edge 33 of the rectangular cross-sectional hole of the fiber-shaft holder 3 and provide an upper stopper for the twisted shaft 4. On the other hand, a lower stopper 34 is placed to block the cylinder part 43 in a downward movement. The function of the upper and lower stoppers is helpful in controlling the movement of the twisted shaft 4, as well as controlling the angular motion of the scanning head 1.

There are many methods in the prior art that are able to provide the power for the mechanism to push and pull the twisted shaft 4 to generate the linear movement. However, hydraulic force, particularly fluidic pressure, is preferred due to the following advantages:

1. Electricity is not required to be transmitted into the scanning head 1 to energize a hydraulic linear mechanism 9. Some of the mechanisms, such as electromagnetic systems (or more particularly, some micro-motors), require not only electricity to be energized, but also additional components, e.g., coils or magnets, installed to the scanning head 1 to transform the electrical energy into mechanical momentum. The use of electricity is not preferable for medical issues; and the requirement of additional components would increase the technical difficulty in manufacturing and the complexity of the whole system. Some of the other mechanisms, like those comprising piezoelectric materials, can be composed with little space and simple structure, but they still need to receive a large voltage to generate the required momentum.

2. A hydraulic mechanism 9 takes little space.

The structure of the hydraulic mechanism 9 is illustrated in FIGS. 18*a* and 18*b*. The hydraulic mechanism 9 can be simply a liquid conduit that guides liquid, such as water, to push or pull the piston system comprised of the cylinder part 43 and the shaft channel 31. Considering that leakage through the gap of a piston system may result in undesirable problems, the hydraulic mechanism 9 is, preferably, comprised of a micro-balloon 91 made by a polymeric thin film. As shown in FIGS. 18*a* and 18*b*, the twisted shaft 4 is in its lower position when the balloon 91 is flat (FIG. 18*a*). As water is pumped into the piston system, the balloon 91 becomes turgid, and the twisted shaft 4 is pushed toward its upper position with an 18 degree spin (FIG. 18*b*). The required back-and forth motion can be generated by switching the flat and turgid states of the micro-balloon 91.

For a single fiber OCT system, a scan rate of 6 rev/sec (6 Hz) is satisfactory [Andrew M. Rollins et al., "Real-time in vivo imaging of human gastrointestinal ultrastructure by use of endoscopic optical coherence tomography with a novel efficient interferometer design", OPTICS LETTERS, Vol. 24, No. 19, Oct. 1, 1999, incorporated by reference herein]. That means in one second the OCT system should be able to provide at least 6 pictures illustrating the cross-sectional data of the vessel. The scanning probe 50 has 20 fibers, so the satisfactory scan rate can be reduced to 0.3 Hz (6÷20=0.3), which is much slower and much easier to be realized by the hydraulic actuating system. Ideally, 15 pictures/sec. is required for optimal image resolution.

Rather than continuous rotation, the scanning probe 50 operates in a back-and-forth manner, so that the angular speed of the scanning head 1 will not be constant even when the whole system reaches its steady state. During operation, therefore, detecting the angle of the scanning head 1, as well as figuring out the angular position that the scanned data belongs to, are important issues. The angle of the scanning head 1 can be simply approximated by comparing the output effort of the pumping system with a reference curve obtained from previous experiments. More precise detection can be reached by the analysis of the feedback of the optical signals. For example, analyzing the Light Doppler Effect [Volker Westphal at al., "Real-time, high velocity-resolution color Doppler optical coherence tomography", OPTICS LETTERS, Vol. 27, No. 1, Jan. 1, 2002, incorporated by reference herein] of the feedback signals is another method.

Figure 20A:
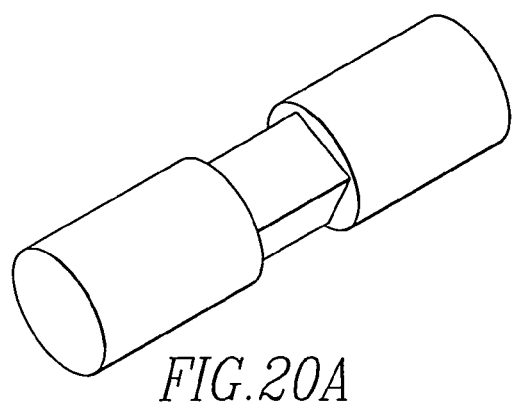
FIGS. 20a-20d are schematic representations of different views of a twisted shaft of the hydraulic mechanism.

The twisted shaft 4 can be formed by precise CNC machining that is well known in the industry. A thin round shaft, minimum diameter 1.0 mm, may be used as the intrinsic material before the machining. For production, two ends of the round shaft are clamped, its central portion is precisely milled and four orthogonal planes on the central portion are generated. The planes define the rectangular cross-section of the twisted shaft 4 (forming a long shaft in this step), as shown in FIG. 20*a*. Following the milling, one of the two clamps holding the shaft is rotated relative to the other clamp to twist the shaft a specific angle about its central axis. The twisted part of the twisted shaft 4 being formed.

Figure 20B:
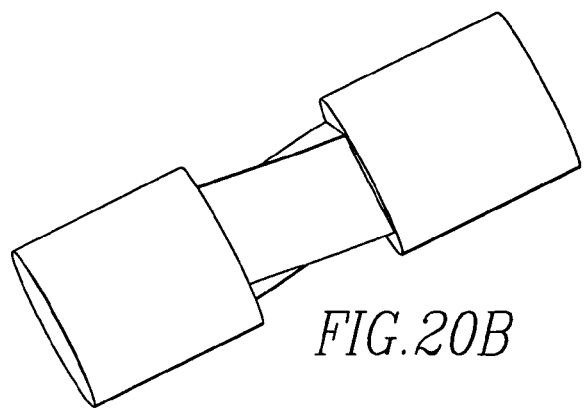

Following the twisting step, the rotated clamp is released to free the elastic distortion of the shaft (with its plastic distortion remaining), and then the clamp is tightened again. At the next step, as shown by FIG. 20*b*, the shaft is milled again at one side of its still-round portion, thereby generating another rectangular portion that is untwisted.

Figure 20C:
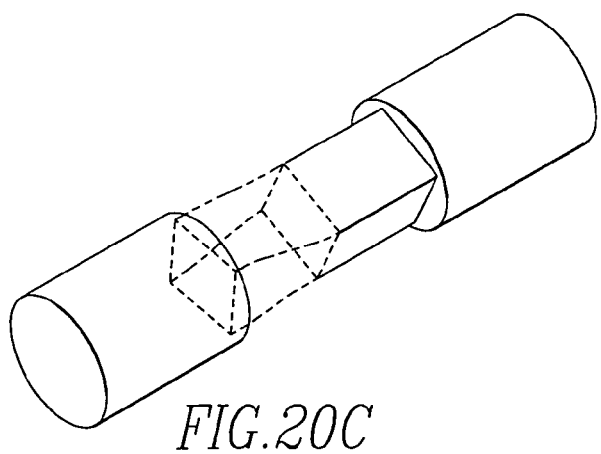
Figure 20D:
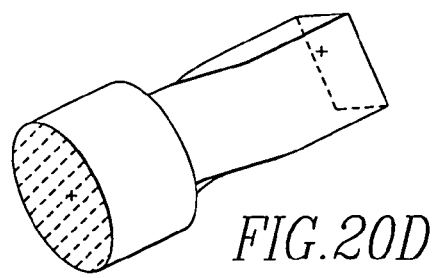

The cylindrical portion (serves as a piston) is formed from the round portion of the shaft. A precise lathering could further be used to fix the central axis and diameter of the cylindrical part. As shown in FIG. 20*c*, only a short portion of the shaft is required. The excess portion of the shaft part is cut off.

Figure 21A:
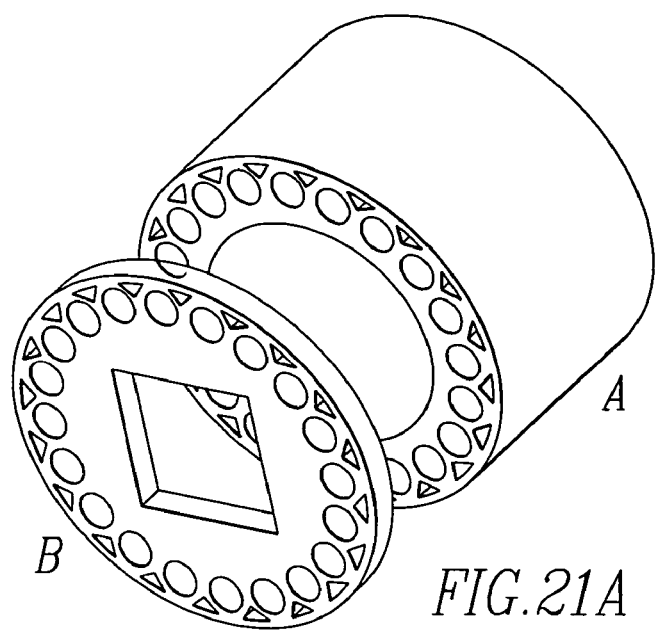
FIGS. 21a and 21b are schematic representations of the fiber-shaft holder.
Figure 21B:
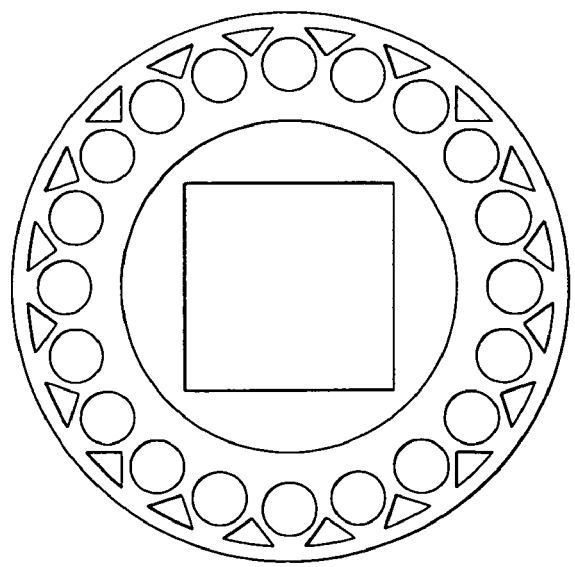
Figure 22A:
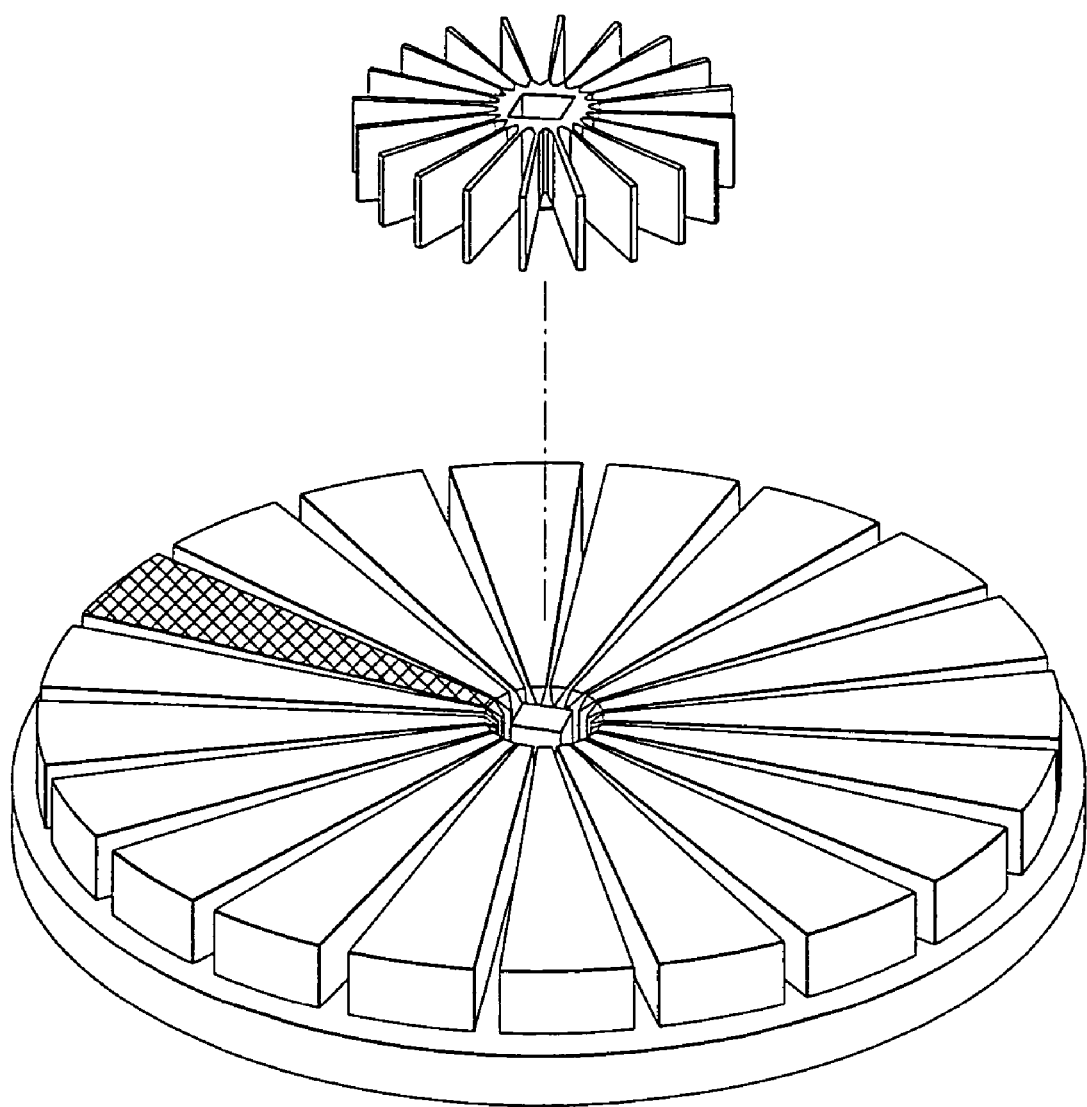
FIGS. 22a-22c are schematic representations of fiber grooves.
Figure 22B:
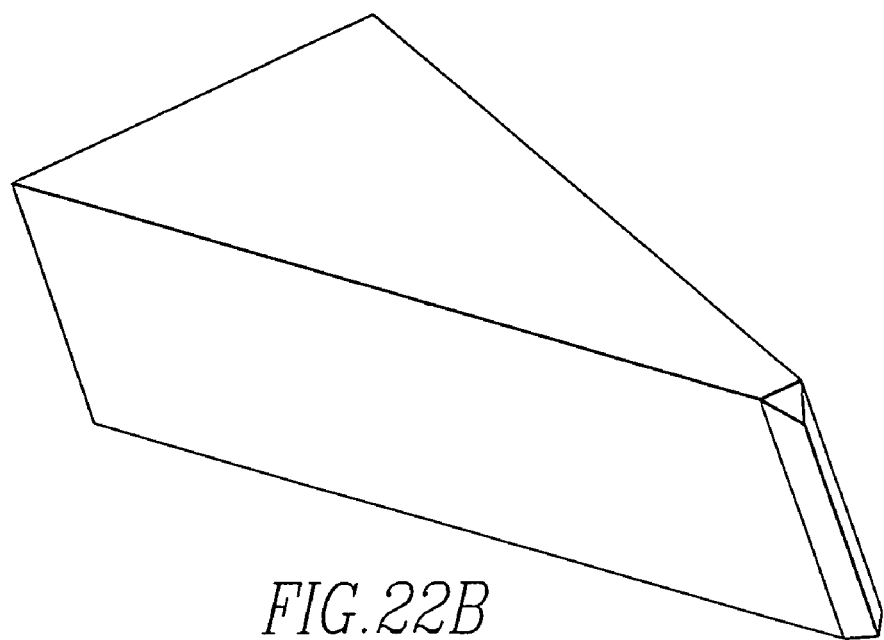
Figure 22C:
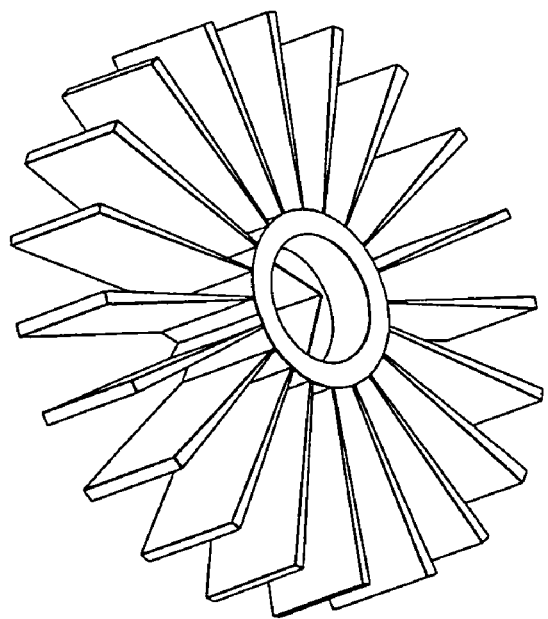

As shown in FIG. 21*a*, the fiber-shaft holder 3 can be combined with two parts, A and B. The part A is actually the body of the catheter. The cross-section of the catheter is shown in FIG. 21*b*; the catheter could be manufactured by the cable extrusion technique that generally is applied in fiber optics industry [Refer to the homepage of Optical Cable Corporation.] Note that the central channel of the catheter is used to be the conduit for the guidance of actuating liquid mentioned previously. There are also several conduits used to guide air flowing in and out the probing tip to balance the air pressure inside the OCT system (during operation, the free volume inside the probing tip changes while the twisted shaft 4 is moving). The diameter of the conduit is equal to that of the cylinder part 43 of the twisted shaft 4.

Part B in FIG. 21*a* is simply a plate having fiber holding edges (B1) and a rectangular central opening (B2). This part could be made from metal by using punching technology as is commonly applied in the industry. In assembly, Part A and Part B are connected with glue such as epoxy. The lower stopper, which is required to constrain the twisted shaft 4 at its lower position, is formed together with the formation of the micro-balloon.

Micro-molding with polymeric material (such as SBS) could be used to fabricate the scanning head 1. The process of micro-molding requires a set of micro-molds. In this case, the fiber grooves 54 and the reflective surface 11 at the end of the fiber grooves 54 can be realized by a set of micro-molds comprised of 18 edges (FIG. 22*a*), each of which has the geometry shown in FIG. 6*b*. As well, the central rectangular channel could be molded by a rectangular shaft made by the equipment for the fabrication of the twisted shaft 4. For the convenience of assembly, the scanning head 1 could be previously provided with the geometry shown in FIG. 22*c*. The excess parts of the scanning head 1 would provide guidance and help with the alignment for the optical fibers 8. UV glue could be used to fix the position of the optical fibers 8. The excess portion of the scanning head 1 could be cut off after the assembly of the optical fibers 8.

Figure 23:
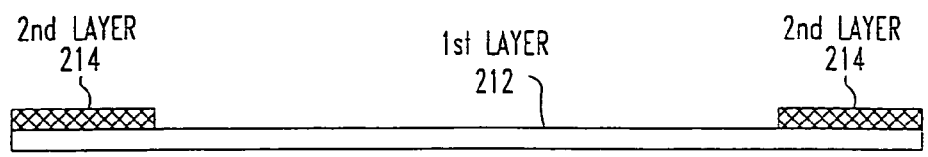
FIG. 23 is a side view of the micro-mirror.
Figure 24:
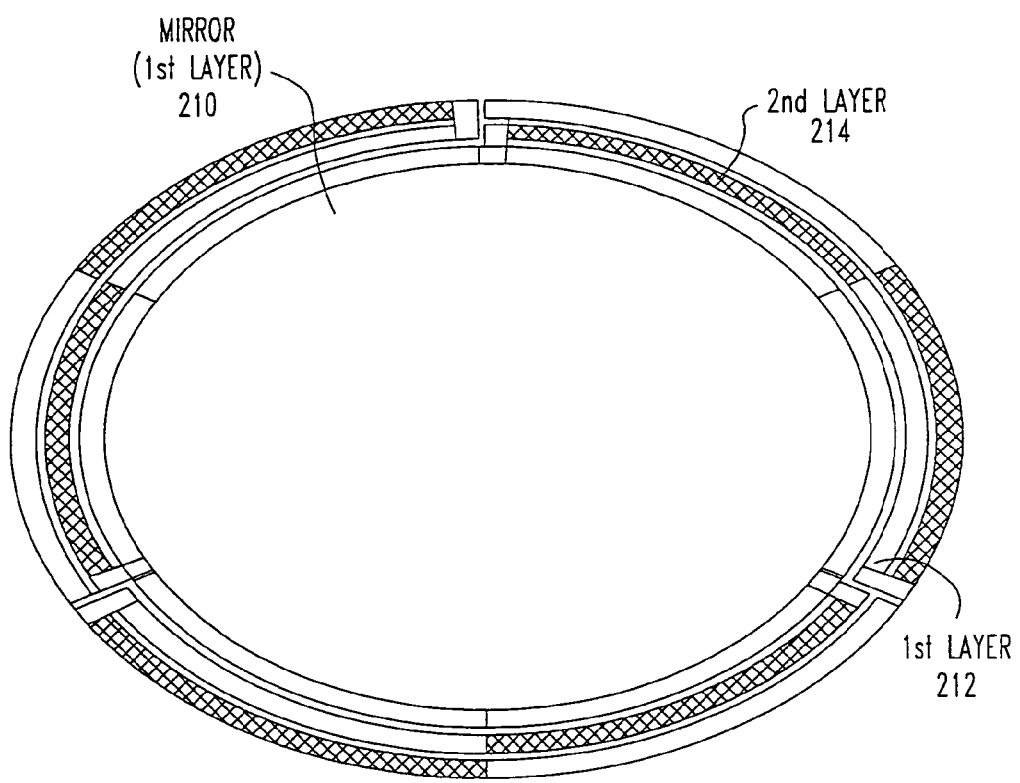
FIG. 24 is a perspective view of the micro-mirror.
Figure 25:
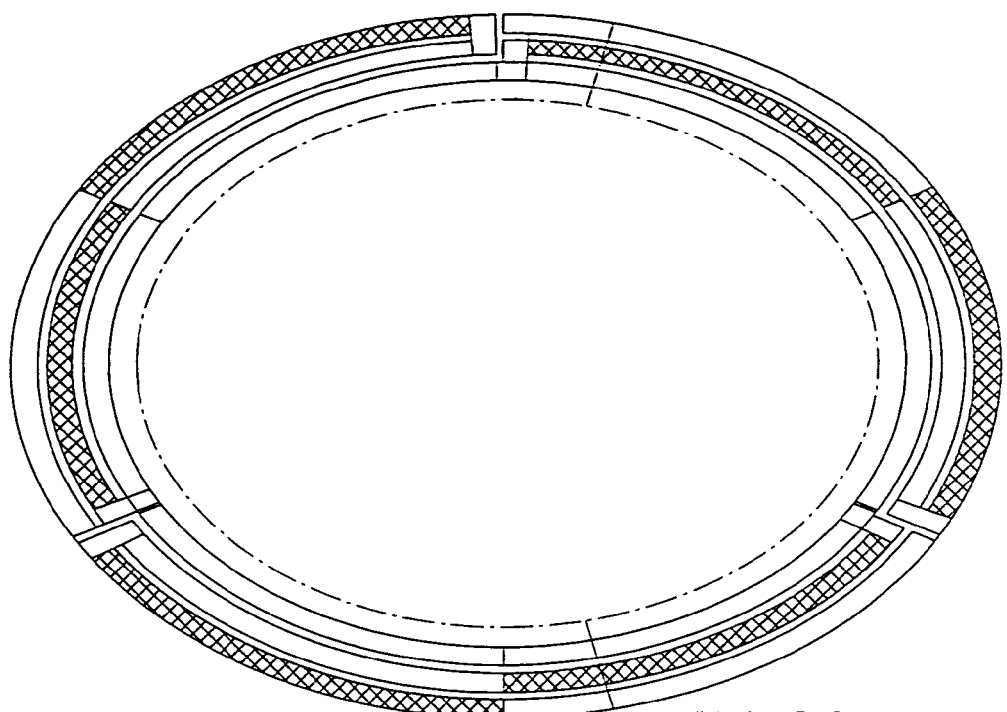
FIG. 25 is a perspective view of the micro-mirror with a portion irradiated by the laser beam.

In another embodiment, laser beams heat at least three different locations on the surface of the micro-mirror 210, which is shown as a disk in FIGS. 23-25, successively. The micro-mirror 210 will provide a wabling corresponding to this kind of un-symmetric heating process, and an incident light (other than the heating laser) can be redirected in a swaying manner.

The heating process corresponds to the rotation period of the micro-mirror 210 as required.

The micro-mirror 210 comprises two layers: a first layer 212 and a second layer 214 (FIG. 23). At least one of the two layers can generate structural deformation (contraction or expansion) by the application of laser light. If the case is that both of the layers are deformable by laser light, the sensitivities of the two layers to a same laser light would be set different to each others. FIG. 24 shows the perspective view of the micro-mirror 210.

When the micro-mirror 210 is irradiated with a laser beam, there will be expansion or contraction in the layers. Because the expansion or contraction within the layers is of different degrees (only one layer is deformed or the two layers are deformed with different degrees), the structure of the whole micro-mirror 210 will be twisted.

Figure 26:
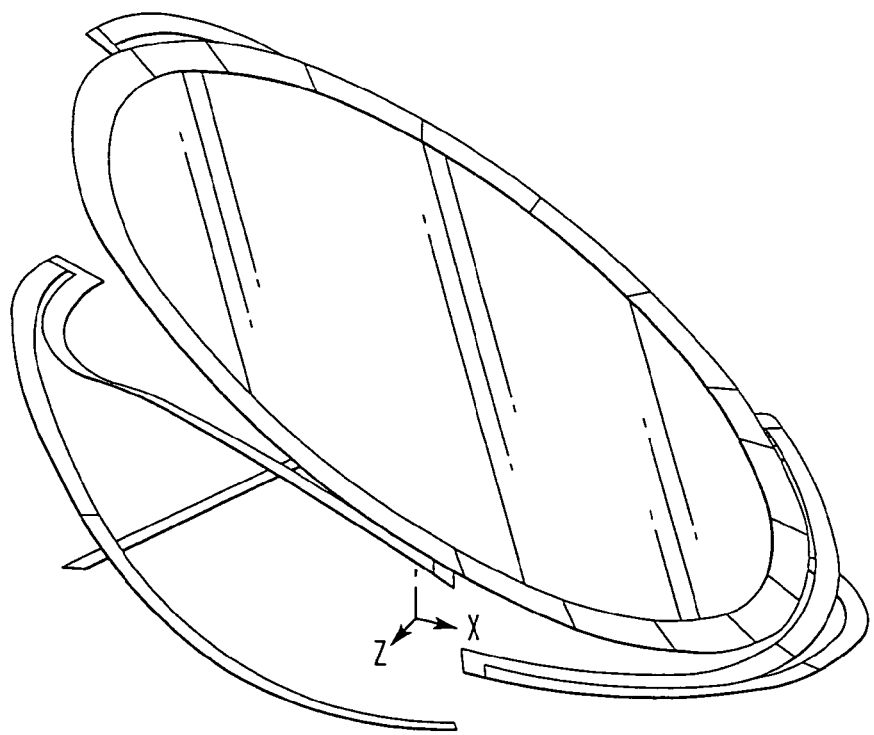
FIG. 26 is a perspective view of the micro-mirror having a deformation generated from being irradiated by a laser beam as shown in FIG. 25.

For example, in FIG. 25, when the section marked with the pie is irradiated with a laser beam, there is a deformation generated as shown in FIG. 26.

The material of the first and second layers 212, 214 could be metals or photosensitive polymers.

In the case of metal layers, for example, the first layer 212 is poly-silicon and the second layer 214 is gold. The mechanism of the expansion or contraction within the layers is thermal expansion. The metals will absorb the energy of a laser beam and be heated. Due to different thermal expansion coefficients of the two layers, the structure will be twisted or bent. This will result in turning the mirror, as shown in FIG. 26.

In the case of photosensitive polymers, for example, liquid crystal materials, the mechanism of the expansion or contraction inside the layers is a phase change of the materials. Under the irradiation of a laser beam, the molecules of the polymeric materials will undergo phase change, wherein the chemical structures of the materials are deformed, and a structural deformation occurs. Next, similar to the case of metal layers, the degrees of deformation of the two layers are different, and there will be a twisting or bending effect in the structure of the micro-mirror 210, and the effect in FIG. 26 is reached.

When the structure is twisted or bent by the application of laser energy, the surface of the mirror, shown in FIG. 24, can be tiled to a specific direction. Therefore, one can control the direction of the micro-mirror 210 by controlling the laser energy input.

The way to control the application of the laser light is to select the location on the micro-mirror 210 to be irradiated by the laser beam, and control the intensity of the laser. By controlling the location, one can control the tilting direction of the mirror; and by controlling the intensity, one can control the tilting angle of the micro-mirror 210.

Figure 27:
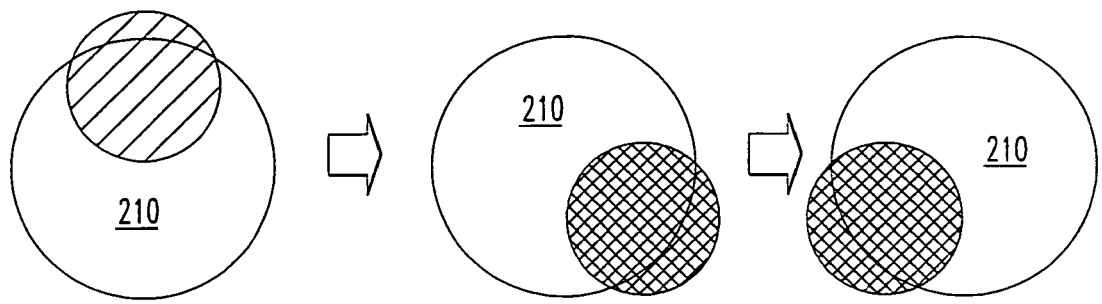
FIG. 27 is a schematic representation of the micro-mirror being continuously heated by a laser beam shining on different locations of the micro-mirror.
Figure 28:
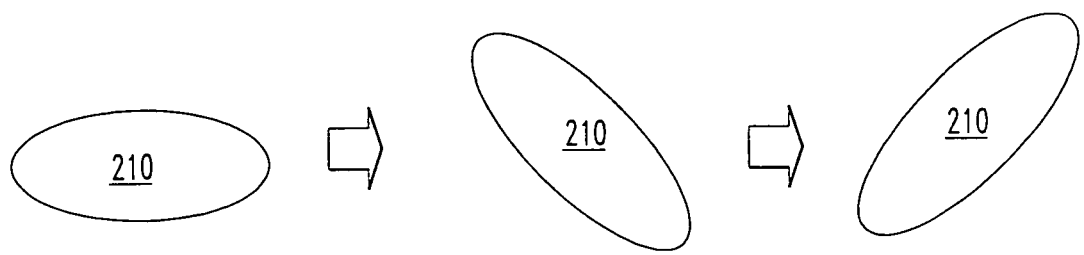
FIG. 28 is a schematic representation of the resulting changing of the tilting direction of the micro-mirror because of the changing location of the laser beam on the micro-mirror.
Figure 29:
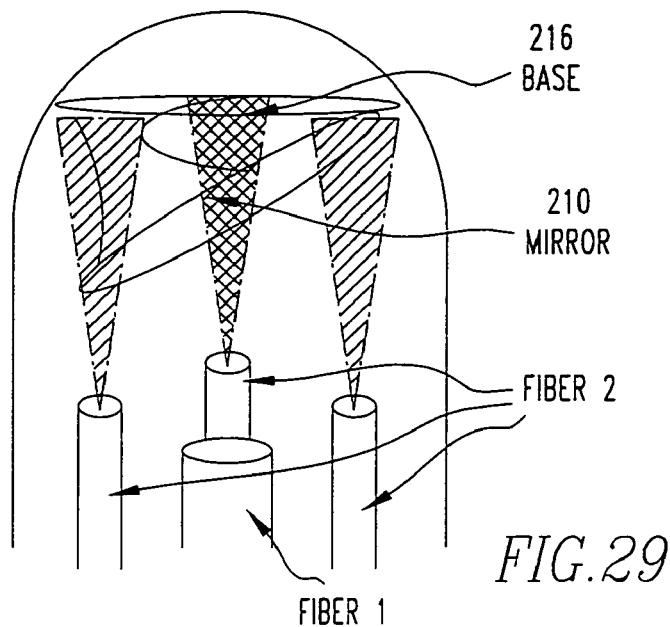
FIG. 29 is a schematic representation of the micro-mirror in the probe cover relative to the fibers.
Figure 30:
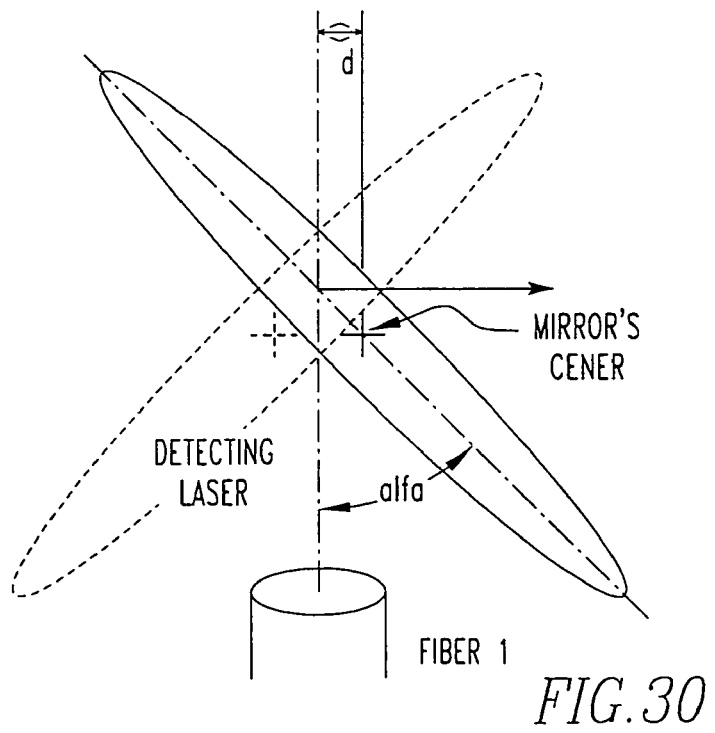
FIG. 30 is a schematic representation of the micro-mirror movement relative to the fiber.

Referring to FIG. 25 and FIG. 26, by continuously changing the laser-shining location (FIG. 27), the tilting direction of the micro-mirror 210 can be continuously changed (FIG. 28). That is, the micro-mirror 210 could be rotated by changing the location of the laser-shining.

This is the mechanism for the rotation of the laser-actuated micro-mirror 210.

As to the assembly of the whole OCT system (FIG. 29), the micro-mirror 210 is mounted on a base 21*b* connected to the tip end of the probe cover. There is no object between the fibers and the mirror. Fiber 1, which is used to guide the detecting light, is the same fiber used in other embodiments of the OCT probe. The detecting light is redirected by the tilting surface of the micro-mirror 210, such that it can scan around by means of the tilting and rotating mirror. The fibers 2 are used to guide the actuating-laser light. As shown, at least three fibers 2 are needed. The fibers 2 fire lasers in turns, such that they can generate continuous tilting effect as shown in FIG. 27 and FIG. 28.

The other features of the laser-actuating OCT probe are the same as those described in other embodiments. For instance, the fiber, and fibers 2 are disposed in a fiber shaft holder 3.

After the fabrication by semiconductor technique, which is well known by those skillful in the art, the mirror is formed on a substrate (usually silicon substrate). The substrate material forms the base. Then a small piece is cut from the base that carries the mirror from the substrate with a dicer. The small piece is mounted on to the tip's end by glue (EPOXY, for example).

Only one fiber 1 is enough to transmit the detecting light in this embodiment. During operation, a circular scanning profile of the detecting laser is realized. In this embodiment, illustrated in FIG. 30, the detecting laser is not centered to the mirror's center. Instead, the following remain constant: (1) d, the distance between the mirror center and the axis of the detecting light. (2) alfa, the angle between the mirror surface and the axis of the detecting light. An open-loop system is used for position feedback to properly arrange the periodical change of the laser powers from the three fibers 2 to realize the constant alfa and d.

The position control is more complex than single-fiber 2 actuation. Particularly, the micro-mirror 210 needs a period of time to respond mechanically to the laser energy coming from the fiber 2. Even though it is known when and which of the fibers 2 are firing the laser power, the exact direction of the mirror surface information cannot be assured.

The absolute position of the mirror is actually not necessary. Instead, speed-control is used to control the rotation of the scanning mirror. For example, in the case of the mirror driven by a transmission cable rotated from outside, the exact position of the mirror (which may be affected by a delay of cable transmission due to the cable's compliance) is not of concern; the rotation period of the mirror is controlled so that the "relative position" of the mirror is known. After receiving a continuous data stream from the reflected detecting laser, the cross-section image of the vessel is constructed by simply matching the data series to the rotating period.

In this embodiment, the operation will be similar. What is different is that the micro-mirror 210 is not actuated by a rotator but by three bimorph heat-deformable cantilever beams. This makes the control more complex. If only one of the fiber 2 fires at one time, it will be very different if not impossible for the mirror to scan a circular profile needed. Instead, the three fibers 2 are needed to fire together, with different powers, to bend the three cantilevers at different status at one time to match a circular scanning profile. The three cantilevers are actuated individually by the three fibers 2 such that they cooperate with specific bending patterns that realize a circular scanning profile on the wall of the vessel.

In an alternative embodiment regarding the micro-mirror 210, the fibers 1 and the fibers 2 are reversed so healing energy comes from a single fiber 2 disposed preferably along the central axis of the tube. The plurality of fibers 1 are disposed about the circumference of the tube. When the micro-mirror 210 is irradiated by the laser beam from the fiber 2, the laser energy causes the mirror to bend. By changing the intensity of the laser or pulsing the laser, motion can be imported to the micro-mirror 210 which wires the probe tip to which it is attached, to move back and forth, and thus the plurality of fibers 1 for scanning the interior of the area of the patient in question.

Thermal expansion material normally can generate ~5% of elongation for a temperature rise of 100° C. The length of the material inside the OCT is originally 20 mm, which can therefore generate a thermal elongation of 1 mm. Polymers, including photosensitive polymers and shape memory polymers are able to generate >100% of photo-induced elongations or shrinkages. The material inside the OCT is originally 1 mm, which can therefore generate a thermal elongation of another 1 mm.

Generally:

Optical tomographic instrumentation may be specified by spectrally resolved bandwidth, which is equivalent to number of spectrally resolvable cells. Each spectrally resolvable cell has a width $\delta v$, such that number of cells resolvable by the instrument is $N_{instrument}=\Delta v/\delta v$, where $\Delta v$ is the available optical bandwidth of source light. The range of group-time delays the optical tomographic instrument can resolve is given by: $\Delta\tau_{instrument}=1/\delta v$. The smallest resolvable group-time delay the optical tomographic instrument can resolve is $\Delta\tau_{coherence}=1/\Delta v$. Number of spectrally resolvable cells the optical tomographic instrument may resolve is given by: $N_{instrument}=\Delta\tau_{instrument}/\Delta\tau_{coherence}$.

For 1 OCT A-scan into the object being imaged, the requirement for number of spectrally resolvable cells is—$N_{A-scan}=\Delta z/L_c$, $L_c\sim c_g/\Delta v$, $\Delta z$=imaging depth, $L_c$ (coherence length), and $c_g$ is the group velocity of light in the object.

$$N_{A-scan}=\Delta\tau_{A-scan}\Delta v$$

Where $\Delta\tau_{A-scan}=\Delta z/c_g$ is the round-trip propagation time for light to propagate from the most superficial and deepest position (to be imaged) in the object.

For some optical tomographic imaging instruments (e.g., those that employ narrow linewidth tunable laser sources or high resolution spectrometers), $N_{instrument}/N_{A-scan}=\Delta\tau_{instrument}$.

The above condition can be stated in three manners: 1) the number of spectrally resolvable cells for the instrument ($N_{instrument}$) is much greater than that required for one A-scan ($N_{A-scan}$); 2) the range of group time delays the instrumentation is capable of resolving ($\Delta\tau_{instrument}$) is much greater than the group-time delay for a single A-scan ($\Delta\tau_{A-scan}$); 3) available optical bandwidth of source light ($\Delta v$) is much greater than spectral width of each resolvable cell of the instrumentation ($\delta v$).

Because the instrument can resolve many more cells than that required for one A-scan, multiplexing techniques are presented here to efficiently utilize the information carrying capacity (bandwidth) afforded by optical tomographic imaging instruments.

Selection criteria of multiplexing techniques employed may be derived in part by the ratio $N_{instrument}/N_{A-scan}=\Delta\tau_{instrument}/\Delta\tau_{instrument}$, multiplexing techniques and more candidate domains (polarization, space, angle, temporal) to multiplex into. Moreover, multiplexing spectral information into just one domain (e.g. spatial) is not the only envisioned approach. Generally, additional spectral information may be resolved into multiple domains (e.g., polarization and spatial).

Specific Implementations:

A. Polarization: The additional spectral cells may be used to record information in the polarization domain using a system indicated in FIG. 31. At least two incident polarization states 90° apart on the Poincare sphere are input into the interferometer. The polarization signature of the light reflected from the sample, such as a vessel wall or nerve fiber layer, is compared to known polarization signatures of materials, such as plaques or a diseased nerve fiber layer. The reflected light and thus the material from which it was reflected is then identified. The fiber delivery system described in PCT patent application number PCT/US2004/012773, incorporated by reference herein, can be used.

The theory of operation of this approach is described using Mueller matrices or the spectrally-resolved Jones calculus. By inserting a FOSPI in the detection path of the spectral domain optical coherence tomography (SD-OCT) instrumentation, the full set of Stokes parameters of light backscattered at the specific depth in the specimen can be obtained without any other polarization controlling components in reference/sample/detection path of the interferometer and the prior knowledge of the polarization state of the light incident on the sample. In this configuration, two factors determine the spectral modulation. One is optical path length difference between the reference and sample surface, ($\Delta(v)$), introduced by the common-path SDOCT and the other is phase retardations, $\phi 1(v)$ and $\phi 2(v)$ generated by the retarder system in the FOSPI. Therefore, output from the presented single channel polarization sensitive (PS)SD-OCT in the time-delay domain is the convolution of the output from FOSPI and that from SD-OCT.

The Stokes parameters of light at the output of the interferometer are $$S_i=S_{i,1}+S_{i,2}+S_{i,i}$$

where the first two terms are the Stokes parameters of light from the reference and sample path, respectively, and the last term is the contribution of interference. Consider the birefringent sample with phase retardation $\delta$ and fast-axis oriented at angle of $\alpha$. Then, the Stokes parameters of the light from the sample ($S_{i,2}$) and interference ($S_{i,i}$) are calculated in terms of the Stokes parameters of light from the reference, $S_{0,1}$, $S_{1,1}$, $S_{2,1}$, $S_{3,1}$.

$$S_{0,2}=r_s^2 S_{0,1}$$

$$S_{1,2}=r_s^2(\cos^2 2\alpha+\cos\delta\sin^2 2\alpha)S_{1,1}+r_s^2(1-\cos\delta)\sin 2\alpha\cos 2\alpha S_{2,1}-r_s^2\sin\delta\sin 2\alpha S_{3,1}$$

$$S_{2,2} = r_s^2(1-\cos\delta)\sin 2\alpha \cos 2\alpha S_{1,1} + r_s^2(\sin^2 2\alpha + \cos\delta \cos^2 2\alpha)S_{2,1} + r_s^2 \sin\delta \sin 2\alpha S_{3,1}$$

$$S_{3,2} = r_s^2 \sin\delta \sin 2\alpha S_{1,1} - r_s^2 \sin\delta \cos 2\alpha S_{2,1} + r_s^2 \cos\delta S_{3,1} \quad (1)$$

$$S_{0,i} = 2r_s\cos\Delta\cos\frac{\delta}{2}S_{0,1} + 2r_s\sin\Delta\sin\frac{\delta}{2}(\cos 2\alpha S_{1,1} + \sin 2\alpha S_{2,1}) \quad (2)$$

$$S_{1,i} = 2r_s\cos\Delta\left(\cos\frac{\delta}{2}S_{1,1} - \sin\frac{\delta}{2}\sin 2\alpha S_{3,1}\right) + 2r_s\sin\Delta\sin\frac{\delta}{2}\cos 2\alpha S_{0,1}$$

$$S_{2,i} = 2r_s\cos\Delta\left(\cos\frac{\delta}{2}S_{2,1} + \sin\frac{\delta}{2}\sin 2\alpha S_{3,1}\right) + 2r_s\sin\Delta\sin\frac{\delta}{2}\cos 2\alpha S_{0,1}$$

$$S_{3,i} = 2r_s\cos\Delta\left(\sin\frac{\delta}{2}\sin 2\alpha S_{1,1} - \sin\frac{\delta}{2}\cos 2\alpha S_{2,1} + \cos\frac{\delta}{2}S_{3,1}\right)$$

with a reflection coefficient of the sample $r_s$ and an optical path length difference between the sample and reference path $\Delta$. Here, the terms including trigonometric functions of $\Delta$ represent the interference between the light from reference and sample paths.

The measured intensity from SDOCT passing through the FOSPI for a birefringent sample, then, is $$I_{out,i}(\nu) = r_s\cos\Delta\cos\frac{\delta}{2}S_{0,1} + r_s\sin\Delta\sin\frac{\delta}{2}(\cos 2\alpha S_{1,1} + \sin 2\alpha S_{2,1}) + \quad (3)$$

$$\frac{1}{2}r_s\left[\left(\cos\frac{\delta}{2}S_{1,1} - \sin\frac{\delta}{2}\sin 2\alpha S_{3,1}\right)\cos(\Delta - \varphi_2) + \sin\frac{\delta}{2}\cos 2\alpha S_{0,1}\sin(\Delta - \varphi_2)\right] +$$

$$\frac{1}{2}r_s\left[\left(\cos\frac{\delta}{2}S_{1,1} - \sin\frac{\delta}{2}\sin 2\alpha S_{3,1}\right)\cos(\Delta + \varphi_2) + \sin\frac{\delta}{2}\cos 2\alpha S_{0,1}\sin(\Delta + \varphi_2)\right] +$$

$$\frac{1}{4}r_s\left[\left(\cos\frac{\delta}{2}S_{2,1} + \sin\frac{\delta}{2}\cos 2\alpha S_{3,1}\right)\cos(\Delta - \varphi_2 + \varphi_1) + \left\{\sin\frac{\delta}{2}\sin 2\alpha(S_{0,1}+S_{1,1}) - \sin\frac{\delta}{2}\cos 2\alpha S_{2,1} + \cos\frac{\delta}{2}S_{3,1}\right\}\sin(\Delta - \varphi_2 + \varphi_1)\right] +$$

$$\frac{1}{4}r_s\left[\left(\cos\frac{\delta}{2}S_{2,1} + \sin\frac{\delta}{2}\cos 2\alpha S_{3,1}\right)\cos(\Delta + \varphi_2 - \varphi_1) + \left\{\sin\frac{\delta}{2}\sin 2\alpha(S_{0,1}+S_{1,1}) + \sin\frac{\delta}{2}\cos 2\alpha S_{2,1} - \cos\frac{\delta}{2}S_{3,1}\right\}\sin(\Delta + \varphi_2 - \varphi_1)\right] -$$

$$\frac{1}{4}r_s\left[\left(\cos\frac{\delta}{2}S_{2,1} + \sin\frac{\delta}{2}\cos 2\alpha S_{3,1}\right)\cos(\Delta + \varphi_2 + \varphi_1) + \left\{\sin\frac{\delta}{2}\sin 2\alpha(S_{0,1}+S_{1,1}) - \sin\frac{\delta}{2}\cos 2\alpha S_{2,1} + \cos\frac{\delta}{2}S_{3,1}\right\}\sin(\Delta + \varphi_2 + \varphi_1)\right]$$

for the interference signal. Fourier transform of equation (3) gives seven components in the positive optical path length difference domain which are centered at $\Delta$, $\Delta \pm \phi_2$, $\Delta \pm (\phi_2 - \phi_1)$, $\Delta \pm (\phi_2 + \phi_1)$, respectively. Inverse Fourier transforms of each component are as follows.

$$\Delta: \frac{1}{2}r_s e^{i\Delta}\left\{\cos\frac{\delta}{2}S_{0,1} - i\sin\frac{\delta}{2}(\cos 2\alpha S_{1,1} + \sin 2\alpha S_{2,1})\right\} \quad (4)$$

$$\Delta + \varphi_2: \frac{1}{4}r_s e^{i\varphi_2}e^{i\Delta}\left\{\left(\cos\frac{\delta}{2}S_{1,1} - \sin\frac{\delta}{2}\sin 2\alpha S_{3,1}\right) - i\sin\frac{\delta}{2}\cos 2\alpha S_{0,1}\right\} \quad (5)$$

$$\Delta + \varphi_2 - \varphi_1: \frac{1}{8}r_s e^{i(\varphi_2 - \varphi_1)}e^{i\Delta}\left[\left(\cos\frac{\delta}{2}S_{2,1} + \sin\frac{\delta}{2}\cos 2\alpha S_{3,1}\right) - i\left\{\sin\frac{\delta}{2}\sin 2\alpha(S_{0,1}-S_{1,1}) + \sin\frac{\delta}{2}\cos 2\alpha S_{2,1} - \cos\frac{\delta}{2}S_{3,1}\right\}\right] \quad (6)$$

$$\Delta + \varphi_2 + \varphi_1: -\frac{1}{8}r_s e^{i(\varphi_2 + \varphi_1)}e^{i\Delta}\left[\left(\cos\frac{\delta}{2}S_{2,1} + \sin\frac{\delta}{2}\cos 2\alpha S_{3,1}\right) - i\left\{\sin\frac{\delta}{2}\sin 2\alpha(S_{0,1}+S_{1,1}) - \sin\frac{\delta}{2}\cos 2\alpha S_{2,1} + \cos\frac{\delta}{2}S_{3,1}\right\}\right] \quad (7)$$

Comparing with equation (2), real part of equation (4) gives $S_{0,i}/4$ and real part of equation of (5) after shifting the phase by $-\phi_2$ gives $S_{1,i}/8$. Likewise, $S_{2,i}/8$ and $S_{3,i}/8$ can be obtained by taking the real part of subtraction of (7) from (6) and the imaginary part of addition of (6) and (7) after the appropriate phase shift, $-(\phi_2 - \phi_1)$ and $-(\phi_2 + \phi_1)$ for (6) and (7), respectively. Moreover, simple arithmetic gives phase retardation due to the birefringence of the sample, $\delta$, without knowledge of incident polarization state. The real part of (4), imaginary part of (5), the imaginary part of subtraction of (7) from (6) are $$\frac{1}{2}r_s\cos\frac{\delta}{2}S_{0,1} \quad (8)$$

$$-\frac{1}{4}r_s\sin\frac{\delta}{2}\cos 2\alpha S_{0,1} \quad (9)$$

$$-\frac{1}{4}r_s\sin\frac{\delta}{2}\sin 2\alpha S_{0,1} \quad (10)$$

after the phase shift by $-\Delta$, $-(\Delta + \phi_2)$, $-(\Delta + \phi_2 - \phi_1)$ and $-(\Delta + \phi_2 + \phi_1)$, respectively. With a trigonometric identity, the following can be obtained $$\tan\frac{\delta}{2} = \frac{2\sqrt{(9)^2 + (10)^2}}{(8)}. \quad (11)$$

Figure 37:
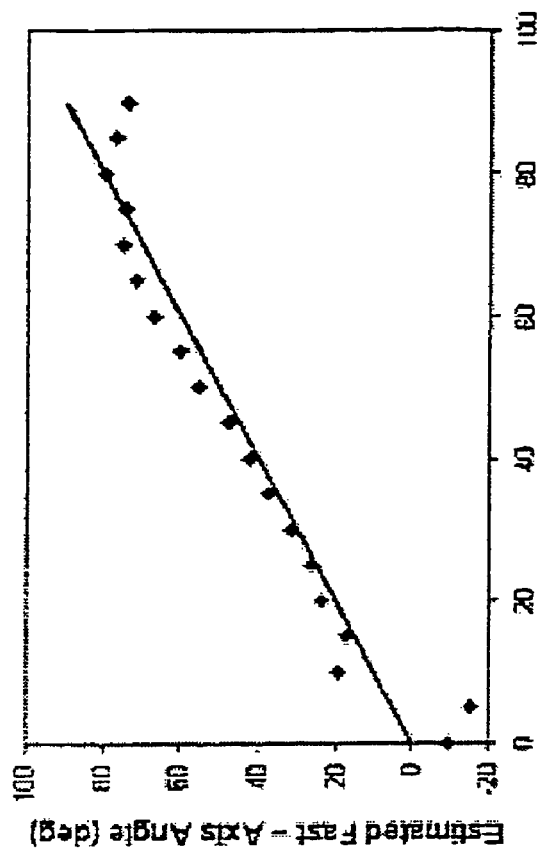
FIGS. 36 and 37 are phase retardation due to birefringence and fast-axis angle, respectively.
Figure 36:
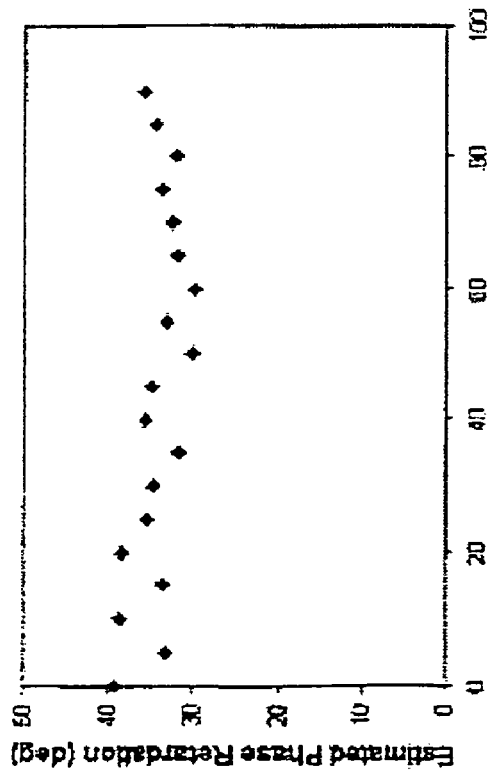

Phase retardation due to birefringence [FIG. 36] and fast-axis angle [FIG. 37] of the birefringent sample were estimated from interference between the back surface of the glass window and the back surface of the birefringent sample by using Eqs. above. For this measurement, the birefringent sample was rotated in 5° increments from 0° to 90°. An estimated single-pass phase retardation of 34.06°±2.68° is consistent with a value deduced from the manufacturer's specification (31.4°). The estimated fast-axis angle is shown in FIG. 4(b) and is plotted with respect to orientation of the birefringent sample.

The results show practical demonstration of polarization multiplexing.

B. Space or Lateral Position: The additional spectral cells may be used to record information in the space or lateral position domain using a system indicated below.

1. Existing Multifiber Approach: (described above)

2. Spatially Scanned Light:

The schematic of the experimental setup of a fiber-based spatially multiplexed swept source OCT (SM-SS-OCT) system is depicted in FIG. 32 using the system described in PCT patent application number PCT/US2004/012773, incorporated by reference herein, where the top is preferably rotated at least 100 times for each position.

Figure 34:
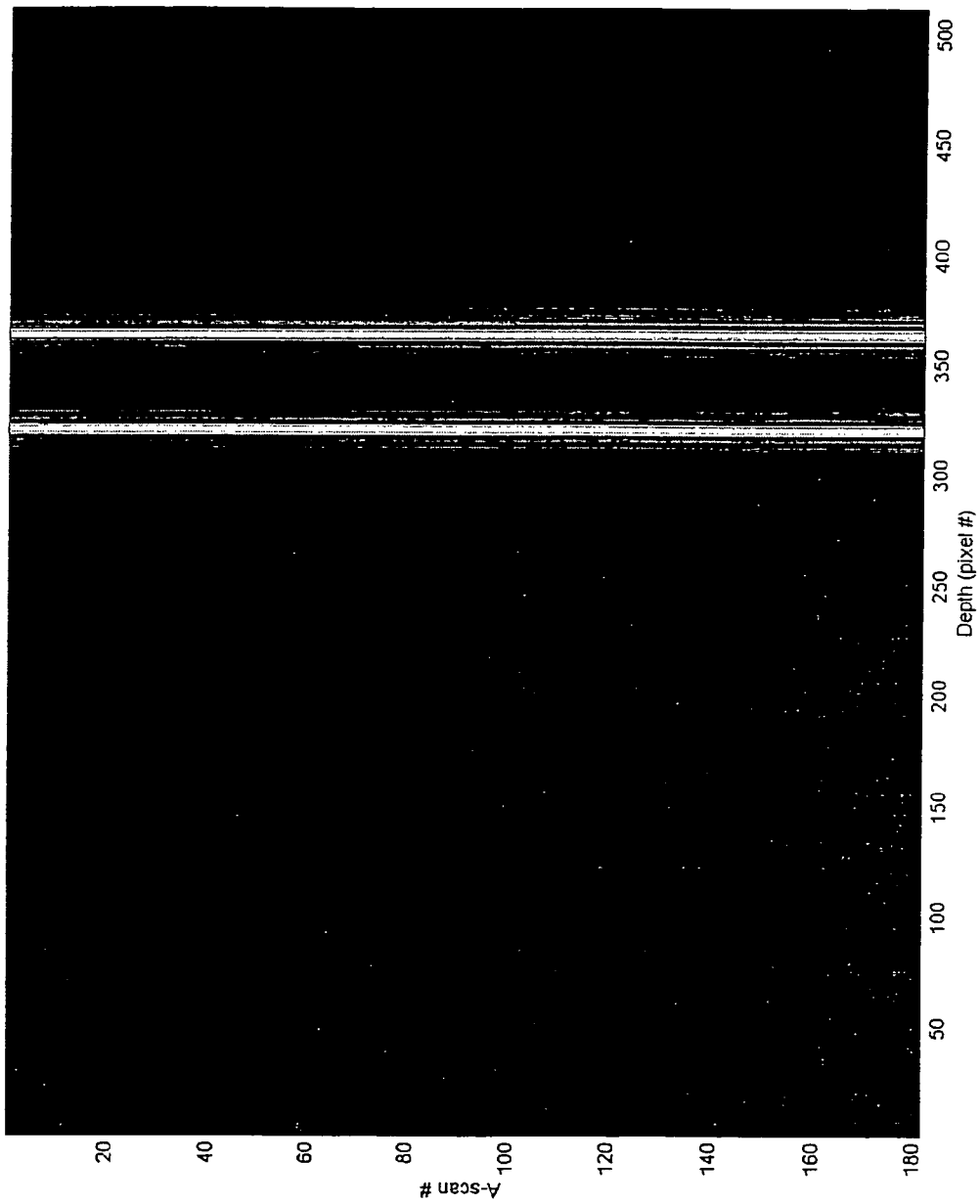
FIGS. 34 and 35 are images recorded with a spatially multiplexed OCT system.
Figure 35:
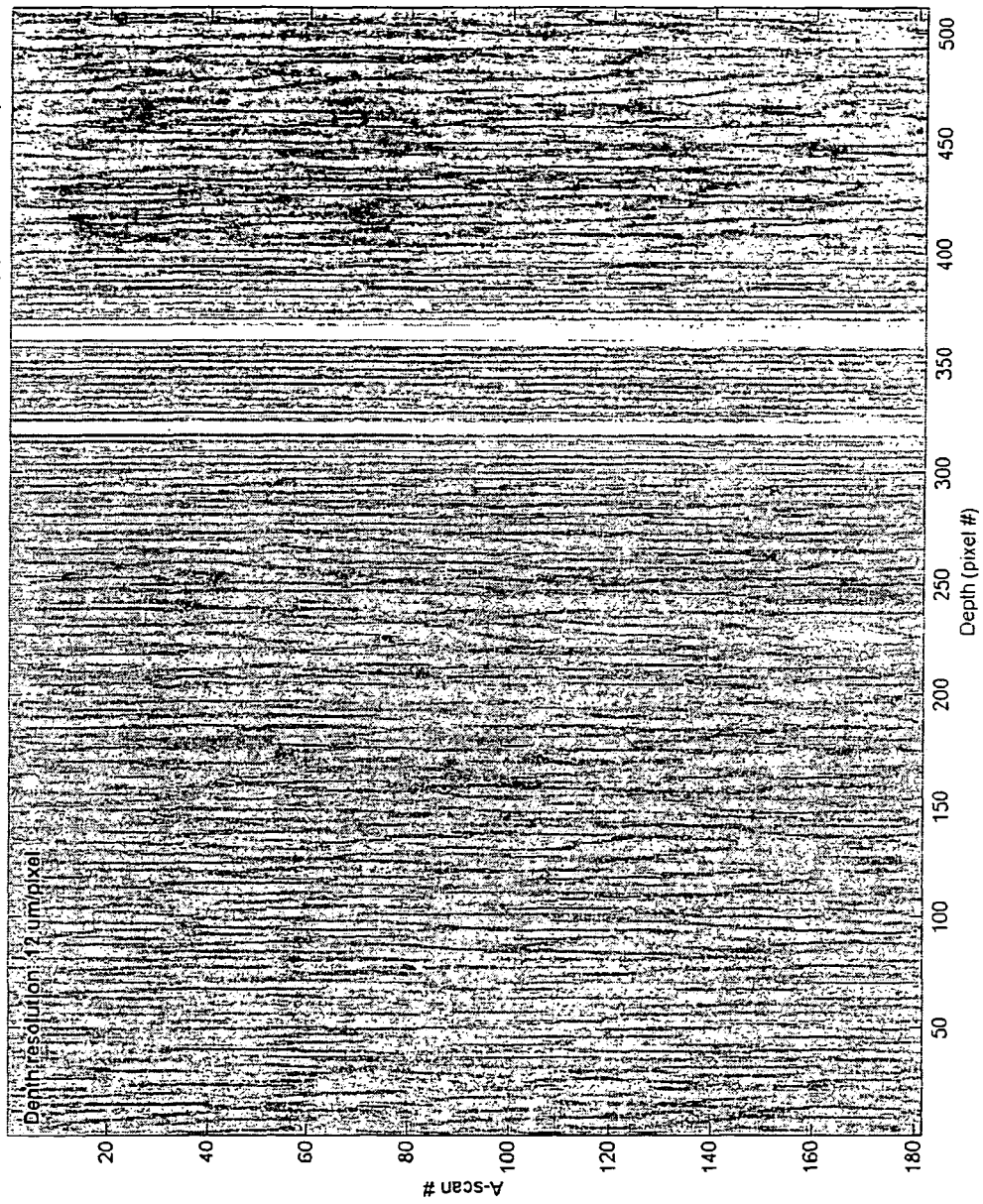

A tunable laser and spectrum analyzer (TLSA 1000, Precision Photonics, Inc.) that operates in the 1520-1620 nm wavelength range ($\lambda_0$=1570 nm) with FWHM spectral line width specified at 150 KHz is used as the illuminating source and is equipped with an optical isolator to protect the laser from spurious reflections. The laser output is coupled into one arm of a 2×2 fiber-based coupler (interferometer). The 50%-50% coupler splits this beam into two nearly equal parts, used in the reference and sample arms, respectively. The reference arm has a fixed path length, and simply consists of a fixed mirror that reflects the entire light incident upon it back into the fiber-based coupler. The light exiting the sample arm of the interferometer is collimated, and scanned across the sample by a scanning galvanometer and a focusing lens. The scanning galvanometer and focusing lens is used to rapidly scan the lateral positions of the tissue. The TLSA 1000 completes one complete wavelength sweep in approximately one second. Within this time, the galvanometer is programmed to sweep all lateral positions of the tissue several hundred times. Light returning from the sample interferes with the light from the fixed reference in the fiber-based interferometer, and the resultant spectral interference signal (due to path length variations between sample and reference reflections) is detected by a photodetector placed in the detection arm of the system. The electrical output is digitized, and a non-uniform Fourier Transform (NUFT) of each A-line spectral data gives the depth profile of the sample reflectance. FIGS. 34 and 35 are images of a 100 micron thick slide recorded with the spatially multiplexed OCT system. The images are of the same object (microscope cover glass) only for one image (FIG. 34) the intensity of the light returning from the sample is displayed on a linear grayscale while in the other image (FIG. 35) is displayed according to logarithm of the intensity.

C. Angle: The additional spectral cells may be used to record information in the angle domain using a system indicated in FIG. 33.

FIG. 33 depicts a Multi Fiber Angle-domain OCT system. The output of the frequency-swept source A is split into n fibers through the splitter B. The light passes through the circulators C, is collimated, focused through a lens, contacts the tissue, and then is reflected into any of the multiplicity of fibers. A reference reflector for each path is introduced into each fiber segment. For example, the reference reflector can be positioned at the terminal end of each fiber segment. For each i'th input fiber segment, interference is formed between light backscattered from the tissue and into the j'th fiber and the reference reflection from the j'th fiber. For N fibers, $N^2$ interference fringes are formed each corresponding to an incident ($\alpha_i$) and backscattered angle ($\beta_j$). Light intensity in the spectral domain is then converted to a voltage through a photoreceiver, which outputs to an ADC board, which is read into a computer. This system allows phase-sensitive angle resolved imaging of discrete light paths in and out-of the specimen. Using a space-spatial frequency transformation (e.g., two-dimensional Fourier transformation) lateral structures can be imaged with sub-wavelength resolution.

D. Space-Angle combinations (e.g. x dimension-space, y dimension-angle): The space and angle dimensions may be combined to form systems that use the additional spectral cells image both space and angles. For example, additional spectral cells may be used to record position information in one dimension (e.g. x) and angle information in the orthogonal dimension (y).

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for studying an object based on at least one of polarization, space, position or angle of light that has reflected from the object comprising:

an optical tomographic instrumentation including a light source coupled to a source path, a sample path, a reference path, and a detection path, wherein the light source generates a spectrally resolved bandwidth; and the spectrally resolved bandwidth includes a plurality of spectrally resolved cells and a detector in the detection path for analyzing light reflected from an object in the sample path and the light reflected in the reference path based upon at least one of the polarization, spatial relationship, position or angle domains, wherein an optical coherence tomography A-scan for the object being imaged is selected by the ratio of $N_{instrument}/N_{A-scan}=\Delta T_{instrument}/\Delta T_{A-scan}$ for the polarization, space, position or angle domain.

2. The apparatus of claim 1, wherein each spectrally resolvable cell includes a width $\delta v$, such that the number of cells resolvable is $N_{instrument}=\Delta v/\delta v$, where $\Delta v$ is the available optical bandwidth of the light source.

3. The apparatus of claim 1, wherein the light source is a linewidth tunable laser.

4. The apparatus of claim 1, wherein a larger ratio of $N_{instrument}/N_{A-scan}=\Delta \tau_{instrument}/\Delta \tau_{A-scan}$ provides a wider selection of multiplexing techniques.

5. The apparatus of claim 1, wherein the optical tomographic instrumentation comprises a spectral domain optical coherence tomography instrumentation, wherein the detection path includes a fiber optic spectral polarimetry instrument, and the detector in the detection path for analyzing light reflected from an object in the sample path and light reflected from the reference path based upon the polarization domain.

6. The apparatus of claim 5, wherein the light source includes at least two incident polarization states that are 90° apart on a Poincare sphere.

7. The apparatus of claim 5, wherein a full set of Stokes parameters of light reflected the object is obtained without any other polarization controlling components in the reference path, the sample path, and the detection path of the spectral domain optical coherence tomography instrumentation.

8. The apparatus of claim 5, wherein the full set of Stokes parameters of light reflected the object is obtained without any other polarization controlling components in the reference path, the sample path, and the detection path of the spectral domain optical coherence tomography instrumentation.

9. The apparatus of claim 1, wherein the optical tomographic instrumentation comprises a swept source optical coherence tomography system; and the detector in the detection path for analyzing light reflected from an object in the sample path and the light reflected from the reference path based upon space or lateral position domain.

10. The apparatus of claim 9, wherein the light source comprises a tunable laser and a spectrum analyzer.

11. The apparatus of claim 10, wherein the tunable laser is output to a coupler to split the output beam of the tunable laser to the reference path and the sample path.

12. The apparatus of claim 11, wherein the light exiting the sample path is collimated by a focusing lens onto the object.

13. The apparatus of claim 12, wherein the detector comprises a photodetector in the detection path to detect a spectral interference signal from the light reflected from the object in the sample path and the light reflected from the reference path.

14. An apparatus for studying an object based on the angle of light reflected from the object comprising: a multi-fiber angle-domain optical coherence tomography system, including a light source coupled to a source path, a reference path, a sample path, and a detection path; and a detector in the detection path for analyzing the light reflected from an object in the sample path and the light reflected from the reference path based upon the angle domain, wherein the light source comprises a frequency swept source split into a plurality of fibers through a splitter and a circulator; the plurality of fibers include at least one sample path to the object and a reference reflector at the terminal end of each of the plurality of fibers; and at least one of an interference fringe is formed from each of the plurality of fibers corresponding to an incident angle ($\alpha_i$) and a backscattered angle ($\beta_j$,) and a light intensity in the spectral domain that is converted to a voltage through a photoreceiver.

15. The apparatus of claim 14, wherein the photoreceiver outputs to an analog-digital converter board.

16. The apparatus of claim 15, wherein the analog-digital converter board outputs to a computer that uses a space-spatial frequency transformation to image lateral structures with sub-wavelength resolution.

17. The apparatus of claim 16, wherein additional spectral cells from the light source and in the plurality of fibers record position information in one dimension and angle information in the orthogonal dimension.

18. A method for studying an object by optical tomographic instrumentation comprising the steps of: providing a spectrally resolved bandwidth of light equivalent to a plurality of spectrally resolvable cells by an optical tomographic instrumentation including a light source coupled to a source path, a reference path, a sample path, and a detection path; and analyzing the light in the detection path that has reflected from the object in the sample path and the light reflected from the reference path based on the polarization, space, position or angle domain, and imaging an optical coherence tomography A-scan for the object being imaged by selecting the ratio of $N_{instrument}/N_{A-scan}=\Delta\tau_{instrument}/\Delta\tau_{A-scan}$ for the polarization, space, position or angle domain.

19. The method of claim 18, wherein each spectrally resolvable cell includes a width $\delta v$, such that the number of cells resolvable the optical tomographic instrument is $N_{instrument}=\Delta v/\delta v$, where $\Delta v$ is the available optical bandwidth of the source light.

20. The method of claim 18, wherein providing a spectrally resolved bandwidth of light further comprises producing light from a spectral domain optical coherence tomography instrumentation, wherein the detection path includes a fiber optic spectral polarimetry instrument; and analyzing the light in the detection path that has reflected from the object in the sample path and the light reflected from the reference path based on the polarization domain.

21. The method of claim 20, further comprising obtaining a full set of Stokes parameters of light reflected the object without any other polarization controlling components in the reference path, the sample path, and the detection path of the spectral domain optical coherence tomography instrumentation.

22. The method of claim 18, wherein providing a spectrally resolved bandwidth of light further comprises producing light from a tunable laser source; and analyzing the light in the detection path that has reflected from the object in the sample path and the light reflected from the reference path based on the space domain.

23. The method of claim 22, wherein the producing light step further comprises outputting the light from the tunable laser to a coupler to split the output beam of the tunable laser to the reference path and the sample path.

24. A method for studying an object with a multi-fiber angle-domain optical coherence tomography system comprising the steps of producing light from a frequency swept source coupled to a source path, a reference path, a sample path, and a detection path; and analyzing the light in the detection path that has reflected from the object in the sample path and the light that has reflected from the reference path based on the angle domain, splitting the output of the frequency swept source into a plurality of fibers through a splitter and a circulator and outputting to the sample path and the reference path in each of the plurality of fibers, wherein the plurality of fibers include at least one sample path to the object and a reference reflector at the terminal end of each of the plurality of fibers; and forming at least one of an interference fringe from each of the plurality of fibers corresponding to an incident angle ($\alpha_i$) and a backscattered angle ($\beta_j$,) and a light intensity in the spectral domain that is converted to a voltage through a photoreceiver.

25. The method of claim 24, further comprising outputting the photoreceiver to an analog-digital converter board and a computer to conduct a space-spatial frequency transformation.

* * * * *